(12) United States Patent
Peddicord

(10) Patent No.: US 11,027,120 B2
(45) Date of Patent: Jun. 8, 2021

(54) URINARY INCONTINENCE TREATMENT DEVICE AND METHOD FOR USING THE SAME

(71) Applicant: INCONTROL MEDICAL, LLC, Brookfield, WI (US)

(72) Inventor: Herschel Peddicord, Longboat Key, FL (US)

(73) Assignee: InControl Medical, LLC, Brookfield, WI (US)

( * ) Notice: Subject to any disclaimer, the term of this patent is extended or adjusted under 35 U.S.C. 154(b) by 37 days.

(21) Appl. No.: 16/145,985

(22) Filed: Sep. 28, 2018

(65) Prior Publication Data

US 2020/0101280 A1    Apr. 2, 2020

(51) Int. Cl.
  *A61N 1/05*    (2006.01)
  *A61N 1/36*    (2006.01)
  *A61M 25/10*    (2013.01)

(52) U.S. Cl.
  CPC ....... *A61N 1/0514* (2013.01); *A61N 1/36007* (2013.01); *A61M 25/1018* (2013.01); *A61N 1/0524* (2013.01); *A61N 1/36003* (2013.01)

(58) Field of Classification Search
  CPC .. A61N 1/0514; A61N 1/0512; A61N 1/0521; A61N 1/0524; A61N 1/36007; A61N 1/36003; A61M 20/1018
  See application file for complete search history.

(56) References Cited

U.S. PATENT DOCUMENTS

| 3,403,684 A | 10/1968 | Stiebel et al. |
|---|---|---|
| 3,626,931 A | 12/1971 | Bysakh |
| 3,800,800 A | 4/1974 | Garbe et al. |
| 3,970,856 A | 7/1976 | Mahaffey et al. |
| 4,106,511 A | 8/1978 | Erlandsson |
| 4,296,760 A | 10/1981 | Carlsson et al. |
| 4,881,526 A | 11/1989 | Johnson et al. |
| 4,909,263 A | 3/1990 | Norris |

(Continued)

FOREIGN PATENT DOCUMENTS

| AU | 2015268783 | 1/2016 |
|---|---|---|
| KR | 10674042 B1 | 1/2007 |

(Continued)

OTHER PUBLICATIONS

Extended European Search Report for European Patent Application No. EP 117964389, dated Apr. 16, 2014, 7 pages.

(Continued)

*Primary Examiner* — Tammie K Marlen
(74) *Attorney, Agent, or Firm* — Foley & Lardner LLP

(57) ABSTRACT

An apparatus for the treatment of urinary incontinence includes a balloon configured for movement between an inflated state and a deflated state, and the balloon includes bellows. An electrode is coupled to an outer surface of the balloon, and is configured to transmit an electrical pulse to cause a contraction of a muscle in communication with the electrode. A control device is configured to be operable by a user to cause the balloon to selectively move between the inflated state and the deflated state and to cause the electrode to transmit the electrical pulse. The bellows and the electrode are configured to cooperate to maintain the structural integrity of the balloon. The bellows and the electrode are further configured to cooperate to cause the balloon to inflate in a radially non-uniform manner.

21 Claims, 12 Drawing Sheets

(56) References Cited

U.S. PATENT DOCUMENTS

| | | |
|---|---|---|
| 4,969,474 A | 11/1990 | Schwarz |
| 5,010,895 A | 4/1991 | Maurer et al. |
| D320,087 S | 9/1991 | Sholzberg et al. |
| 5,103,809 A | 4/1992 | Deluca et al. |
| 5,199,443 A | 4/1993 | Maurer et al. |
| 5,314,465 A | 5/1994 | Maurer et al. |
| 5,370,671 A | 12/1994 | Maurer et al. |
| 5,376,064 A | 12/1994 | Cerny |
| 5,377,692 A | 1/1995 | Pfeil |
| 5,385,577 A | 1/1995 | Maurer et al. |
| 5,529,574 A | 6/1996 | Frackelton |
| 5,562,717 A | 10/1996 | Tippey et al. |
| D384,156 S | 9/1997 | Kain |
| 5,662,699 A | 9/1997 | Hamedi et al. |
| 5,702,428 A | 12/1997 | Tippey et al. |
| 5,733,230 A | 3/1998 | Sawchuck et al. |
| 5,800,501 A | 9/1998 | Sherlock |
| 5,875,778 A | 3/1999 | Vroegop |
| 5,881,731 A | 3/1999 | Remes |
| D414,871 S | 10/1999 | Myers et al. |
| 6,139,569 A | 10/2000 | Ingle et al. |
| 6,190,307 B1 | 2/2001 | Tsai |
| 6,289,894 B1 | 9/2001 | Remes |
| 6,488,673 B1 | 12/2002 | Laufer et al. |
| 6,625,495 B1 | 9/2003 | Alon et al. |
| 6,741,895 B1 | 5/2004 | Gafni et al. |
| 6,905,471 B2 | 6/2005 | Leivseth et al. |
| 7,079,882 B1 | 7/2006 | Schmidt |
| 7,104,950 B2 | 9/2006 | Levy |
| D530,822 S | 10/2006 | Inubushi |
| D536,097 S | 1/2007 | Nan |
| D536,797 S | 2/2007 | Klearman et al. |
| D546,964 S | 7/2007 | Wu |
| D555,798 S | 11/2007 | Nan |
| D555,799 S | 11/2007 | Nan |
| D558,356 S | 12/2007 | Nan |
| 7,341,566 B2 | 3/2008 | Nan |
| D579,573 S | 10/2008 | Nan |
| 7,438,681 B2 | 10/2008 | Kobashikawa et al. |
| D585,560 S | 1/2009 | Wu |
| D592,758 S | 5/2009 | Kain |
| 7,534,203 B2 | 5/2009 | Gil |
| 7,577,476 B2 | 8/2009 | Hochman et al. |
| D603,523 S | 11/2009 | Nan et al. |
| D606,206 S | 12/2009 | Nan et al. |
| D606,207 S | 12/2009 | Nan et al. |
| D606,208 S | 12/2009 | Nan et al. |
| D615,663 S | 5/2010 | Nan |
| 7,845,985 B2 | 12/2010 | Brunker et al. |
| D636,888 S | 4/2011 | Nikitczuk et al. |
| 7,931,605 B2 | 4/2011 | Murison |
| 7,957,794 B2 | 6/2011 | Hochman et al. |
| D643,128 S | 8/2011 | Mohamed et al. |
| 7,998,057 B2 | 8/2011 | Kain |
| D648,442 S | 11/2011 | Caggiano et al. |
| D652,526 S | 1/2012 | Peddicord |
| D653,350 S | 1/2012 | Chen |
| D669,592 S | 10/2012 | Peddicord |
| D669,997 S | 10/2012 | Crockford |
| D670,398 S | 11/2012 | Peddicord |
| D670,399 S | 11/2012 | Peddicord |
| D674,503 S | 1/2013 | Peddicord |
| 8,369,953 B2 | 2/2013 | Peddicord |
| D682,436 S | 5/2013 | Lowsky |
| 8,509,900 B2 | 8/2013 | Boyd et al. |
| 8,784,345 B2 | 7/2014 | Peddicord |
| 8,805,509 B2 | 8/2014 | Boyd et al. |
| 8,818,512 B2 | 8/2014 | Peddicord |
| D716,763 S | 11/2014 | Niho et al. |
| D723,709 S | 3/2015 | Topolovac et al. |
| 9,655,808 B2 | 5/2017 | Peddicord |
| 2003/0083590 A1 | 5/2003 | Hochman et al. |
| 2004/0030360 A1 | 2/2004 | Eini et al. |
| 2004/0054392 A1 | 3/2004 | Dijkman |
| 2004/0082859 A1 | 4/2004 | Schaer |
| 2007/0118058 A1 | 5/2007 | Isshiki |
| 2007/0149903 A1 | 6/2007 | Nan |
| 2007/0185417 A1 | 8/2007 | Mittal et al. |
| 2008/0009775 A1 | 1/2008 | Murison |
| 2008/0103519 A1 | 5/2008 | Bonutti |
| 2008/0119767 A1 | 5/2008 | Berry et al. |
| 2008/0262529 A1 | 10/2008 | Jacques |
| 2009/0005714 A1 | 1/2009 | Mecenero |
| 2009/0030266 A1 | 1/2009 | Treanor |
| 2009/0069730 A1 | 3/2009 | Knyrim |
| 2009/0093673 A1 | 4/2009 | Lee |
| 2009/0171144 A1 | 7/2009 | Squicciarini |
| 2009/0177029 A1 | 7/2009 | Alilovich |
| 2009/0222058 A1 | 9/2009 | Craggs |
| 2009/0222060 A1 | 9/2009 | Boyd et al. |
| 2009/0228064 A1 | 9/2009 | Boyd et al. |
| 2009/0228067 A1 | 9/2009 | Boyd et al. |
| 2009/0270963 A1 | 10/2009 | Pelger et al. |
| 2009/0275796 A1 | 11/2009 | Gil |
| 2009/0281397 A1 | 11/2009 | Lavoisier |
| 2010/0004707 A1 | 1/2010 | Hochman et al. |
| 2010/0041944 A1 | 2/2010 | Levy |
| 2010/0087703 A1 | 4/2010 | Gabrielidis |
| 2010/0087757 A1 | 4/2010 | Hoffman et al. |
| 2010/0106216 A1 | 4/2010 | Cha et al. |
| 2010/0174136 A1 | 7/2010 | Shim |
| 2010/0174137 A1 | 7/2010 | Shim |
| 2010/0174213 A1 | 7/2010 | Shim |
| 2010/0174218 A1 | 7/2010 | Shim |
| 2011/0034834 A1 | 2/2011 | Lapi |
| 2011/0034837 A1 | 2/2011 | Lee |
| 2011/0054513 A1 | 3/2011 | Pepper et al. |
| 2011/0105837 A1 | 5/2011 | Lee |
| 2011/0230802 A1 | 9/2011 | Nan |
| 2011/0230931 A1 | 9/2011 | Hagege |
| 2012/0215141 A1 | 8/2012 | Peddicord |
| 2012/0215280 A1 | 8/2012 | Peddicord |
| 2012/0265044 A1 | 10/2012 | Broens |
| 2013/0261702 A1 | 10/2013 | Garfield et al. |
| 2014/0200646 A1 | 7/2014 | Boyd et al. |
| 2017/0252264 A1 | 9/2017 | Peddicord |

FOREIGN PATENT DOCUMENTS

| | | |
|---|---|---|
| KR | 100895220 | 4/2009 |
| RU | 2132152 | 6/1999 |
| WO | WO-2010/067360 A2 | 6/2010 |

OTHER PUBLICATIONS

International Search Report and Written Opinion for Application No. PCT/US2011/040714, dated Feb. 17, 2012, 9 pages.

Patent Examination Report No. 1 for Australian Patent Application No. 2011268245, dated Mar. 18, 2014, 4 pages.

Search Report from the Russian Application No. 2016122910, dated Jul. 27, 2017, 2 pages.

Office Action from the Russian Application No. 2016122910, dated Jun. 27, 2018, 5 pages.

URINARY INCONTINENCE TREATMENT DEVICE AND METHOD FOR USING THE SAME

BACKGROUND

The present disclosure relates generally to the field of nerve and muscle stimulation. One aspect of the present disclosure relates to a device and method for electronic nerve and muscle stimulation, and in particular, internal tissue stimulation. The present disclosure relates specifically a device and method for various medical applications, including the treatment of urinary incontinence in females.

Urinary incontinence in females has numerous causes but is frequently tied to the weakening of pelvic floor muscles. Some studies have indicated a high success rate at relieving incontinence symptoms by strengthening pelvic floor muscles. Certain exercises may be performed to strengthen muscles in this area. However, the efficacy of daily exercises is dependent on patient compliance with the prescribed exercise regimen and patient compliance with the exercise regimen may be poor.

SUMMARY

One embodiment relates an apparatus for the treatment of urinary incontinence including a balloon, an electrode, and a control device. The balloon is configured for movement between an inflated state and a deflated state. The balloon includes bellows. The electrode is coupled to an outer surface of the balloon, and is configured to transmit an electrical pulse to cause a contraction of a muscle in communication with the electrode. The control device is configured to be operable by a user to cause the balloon to selectively move between the inflated state and the deflated state and to cause the electrode to transmit the electrical pulse. The bellows and the electrode are configured to cooperate to maintain the structural integrity of the balloon. The bellows and the electrode are further configured to cooperate to cause the balloon to inflate in a radially non-uniform manner.

Another embodiment relates to an apparatus for the treatment of urinary incontinence including a balloon, a first electrode, a second electrode, and a control device. The balloon is configured for movement between an inflated state and a deflated state. The balloon includes bellows. The first electrode is coupled to a first outer surface of the balloon. The first electrode is configured to transmit an electrical pulse to cause a contraction of a muscle in communication with the first electrode. The second electrode is coupled to a second outer surface of the balloon. The second electrode is configured to transmit an electrical pulse to cause a contraction of a muscle in communication with the second electrode. The control device is configured to cause the balloon to inflate such that the first electrode and the second electrode contact the muscle, and to cause the first electrode and the second electrode to transmit electrical pulses to the muscle. The balloon is substantially hollow. The bellows, the first electrode, and the second electrode are configured to cooperate to maintain the structural integrity of the balloon.

Another embodiment a method for treating urinary incontinence. The method includes providing a device including a balloon, a first electrode, and a second electrode. The balloon is configured for movement between an inflated state and a deflated state. The balloon includes bellows. The first electrode is coupled to a first outer surface of the balloon. The first electrode is configured to transmit an electrical pulse to cause a contraction of a muscle in communication with the first electrode. The second electrode is coupled to a second outer surface of the balloon. The second electrode is configured to transmit an electrical pulse to cause a contraction of a muscle in communication with the second electrode. The method further includes causing, by a control device, the balloon to inflate such that the first electrode and the second electrode contact the muscle. The method further includes causing, by the control device, the first electrode and the second electrode to transmit electrical pulses to the muscle. The balloon is substantially hollow. The bellows, the first electrode, and the second electrode are configured to cooperate to maintain the structural integrity of the balloon.

DETAILED DESCRIPTION

Figure 1:
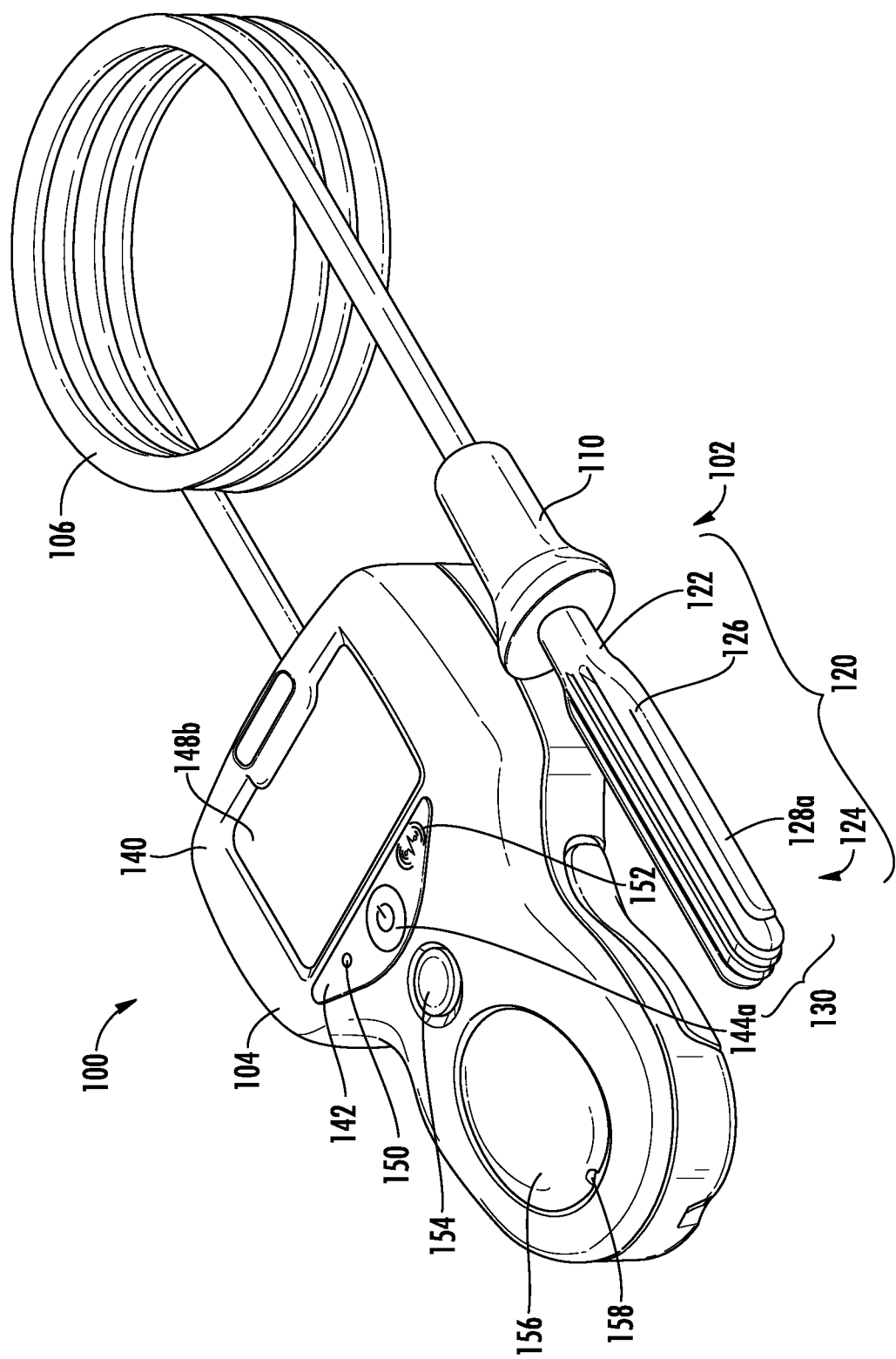
FIG. 1 is a perspective view of a medical device, shown according to an exemplary embodiment.

Referring generally to the Figures, a medical device and method of treatment are shown according to exemplary embodiments. According to the embodiments shown, the medical device 100 generally includes a probe assembly 102 including a handle 110 and a probe 120. The probe 120 is configured for insertion into a vagina and a rectum. A controller 104 is interconnected with the handle 110 and configured to control operation of the probe 120. The probe 120 includes an inflatable member or balloon 124 on the outer surface of which at least one electrode 128 is disposed. An inflation device may be located in the controller 104 and configured to cause the balloon 124 to inflate, in turn causing at least one of the electrodes 128 to press against at least one vaginal or rectal wall. The balloon 124 may be inflated to a plurality of different inflated positions between fully deflated and fully inflated. The controller 104 includes processing electronics 800 configured to control the electrodes 128 such that the electrodes 128 cause a contraction of a muscle in communication with an electrode 128. The processing electronics 800 are also configured to control inflation and deflation of the balloon 124.

According to an exemplary embodiment, the device and method for treating incontinence deliver electrical pulses to stimulate muscle contraction to strengthen the muscles in the area of the pelvic floor. Electrical stimulation causes muscles to contract and release repeatedly, thereby strengthening those muscles. Urinary incontinence in general, and urinary incontinence in females specifically, may be treated by strengthening the muscles that are responsible for bladder control (e.g., the pelvic floor muscles) using internal electrical stimulation. While the method and device are described for the treatment of urinary incontinence, it is contemplated that this device may also be used for other medical purposes, for example, bowel incontinence, in which case references to a vagina would correspondingly refer to an anus and/or rectum. Persons skilled in the art can also adapt the method and device for other internal applications through other natural orifices or through surgically created orifices.

Before discussing further details of the devices, it should be noted that references to "front," "rear," "right," and "left" in this description are merely used to identify the various elements as they are oriented in the Figures, with "right," "left," "front," and "rear" being relative to a specific direction. These terms are not meant to limit the element which they describe, as the various elements may be oriented differently in various applications.

It should further be noted that for purposes of this disclosure, the term coupled means the joining of two members directly or indirectly to one another. Such joining may be stationary in nature or moveable in nature and/or such joining may allow for the flow of fluids, electricity, electrical signals, or other types of signals or communication between the two members. Such joining may be achieved with the two members or the two members and any additional intermediate members being integrally formed as a single unitary body with one another or with the two members or the two members and any additional intermediate members being attached to one another. Such joining may be permanent in nature or alternatively may be removable or releasable in nature.

Referring to FIG. 1, a perspective view of a device 100 is shown according to an exemplary embodiment. As described herein, device 100 may be used for the treatment of urinary incontinence, specifically in women. According to the exemplary embodiment shown, device 100 includes a probe assembly 102 which includes a housing, shown as handle 110, and a probe 120. Handle 110 provides the user a region which may be grasped for control and manipulation of the probe assembly 102. Handle 110 may facilitate insertion, positioning, and removal of probe 120. Handle 110 is shown to include a sleeve 112 configured to cover the majority of handle 110. Sleeve 112 can be pliable. Sleeve 112 provides a smooth and watertight surface to handle 110. The smooth and watertight surface facilitates cleaning which is beneficial due to the handle's 110 proximity to bodily fluids and the vaginal opening during use. Sleeve 112 may be translucent to allow lights (e.g., lamps, LEDs, displays, etc.) within handle 110 to shine through. Further, sleeve 112 may be customizable, e.g., bearing various colors or logos. Sleeve 112 can be formed from various materials, such as silicone rubber.

According to the embodiment shown, probe 120 generally has the form of an elongated cylinder having an open proximal end and a closed distal end. Probe 120 may include a neck portion 122 near the proximal end. Probe 120 includes a member or expandable portion, shown as balloon 124. According to the exemplary embodiment, balloon 124 includes a single inflatable balloon having an outer surface 126. According to alternate embodiments, the expandable portion may include a plurality of balloons. According to various embodiments, the plurality of balloons may be oriented axially, radially, circumferentially, or some combination thereof. Balloon 124 may be formed of an airtight, elastic, biocompatible material, such as silicone rubber. However, it will be appreciated that balloon 124 may be formed of any suitable material.

Figure 3:
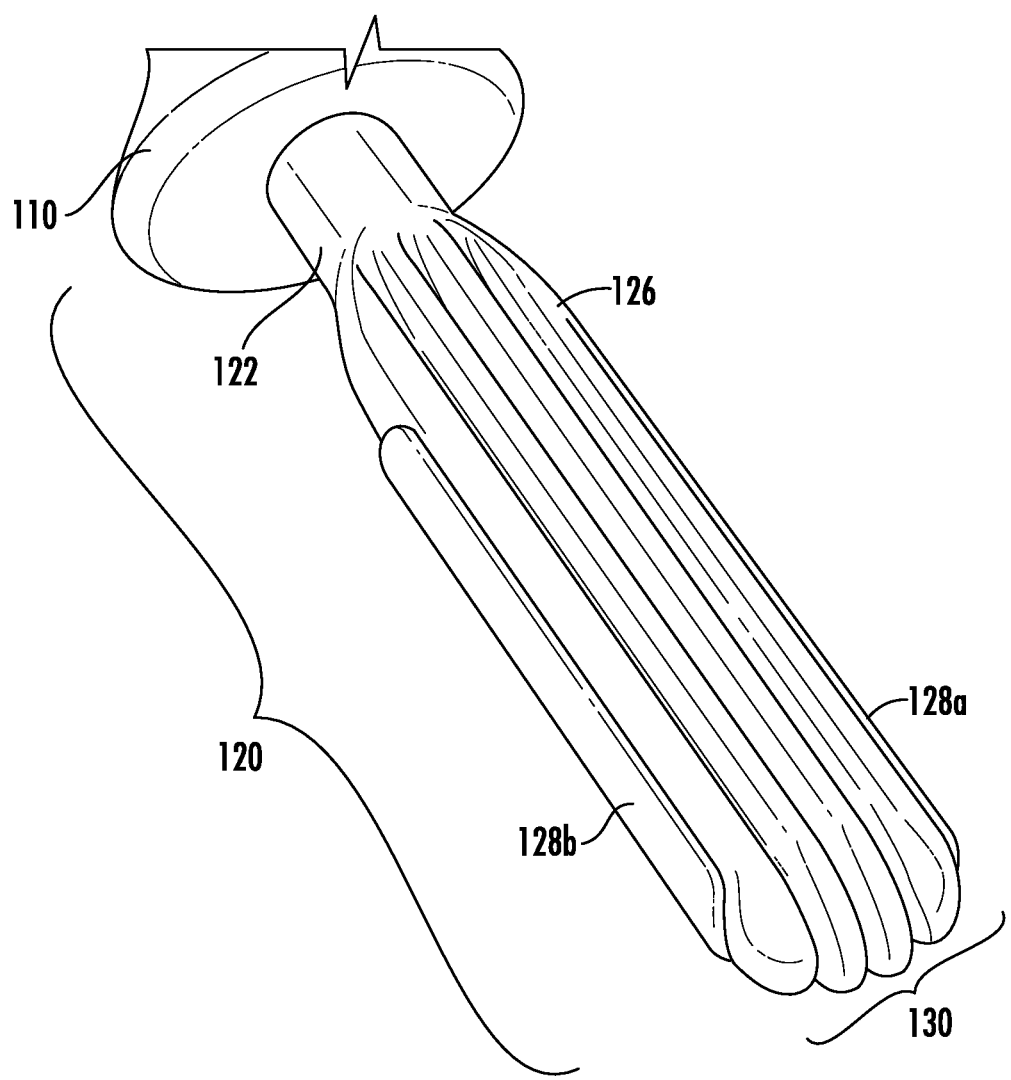
FIG. 3 is a perspective view of a probe of the medical device of FIG. 1, shown according to an exemplary embodiment.

Probe 120 is further shown to include at least one electrode 128, shown as electrode 128a (e.g., first electrode, right electrode, etc.). Preferably, electrode 128 is mounted to outer surface 126 of balloon 124 in such a manner that electrode 128 may come into contact with tissue adjacent to balloon 124 when probe 120 is in an inserted position. Referring briefly to FIG. 3, probe 120 may include a second electrode 128b (e.g., left electrode, etc.). First electrode 128a and second electrode 128b are shown radially opposite one another; however, probe 120 may have a plurality of electrodes 128, the plurality of electrodes being located anywhere on probe 120, e.g., top and bottom sides, both on top, axially or circumferentially offset, or equally or unequally spaced circumferentially around probe 120. The relative position of the electrodes 128 is dependent upon the particular tissue to receive the electrical stimulation. The placement and relative spacing of the electrodes will determine, in part, the effectiveness of the muscle contraction as a result of the electrical stimulation. According to various embodiments, a plurality of electrodes may be energized at the same time, different electrodes (e.g., a subset of a plurality of electrodes) may be actuated during different phases of a treatment session, or different electrodes may be actuated during different treatment sessions. For example, an even number of electrodes 128 may be actuated in pairs, or an odd number of electrodes may be actuated in a rotating pattern. Actuating different electrodes 128 at different times may cause different muscles to contract, thereby strengthening more and different pelvic floor muscles and preventing the muscles from becoming adjusted or de-sensitized to the electrical stimulation. The plurality of electrodes 128 may have the same or different shape. Electrode 128 is configured to deliver electrical pulses (e.g., signals, currents, voltages, frequencies, etc.) to stimulate muscle contraction to strengthen the muscles in the area of the pelvic floor. Electrode 128 may also communicate a response information (e.g., a signal indicative of the contractive force of the muscles) to processing electronics. According to one embodiment, the response information is a voltage created by the contracting muscle. According to another embodiment, the response information is an electric potential difference between first electrode 128a and second electrode 128b. The muscle contraction causing the response information may be caused by electrode stimulation of the muscle or may be the result of a manual contraction caused by the user.

According to the exemplary embodiment, electrodes 128 may be formed from stainless steel, and in another embodiment, the electrodes may be formed from an expandable, conductive silicone rubber or any other suitable material. It may be desirable to limit electrodes 128 from expanding so as to maintain a relatively consistent conductivity or to prevent the muscle stimulation from moving as balloon 124 is expanded. Further, electrodes formed of materials different than balloon 124 may not expand at the same rate as balloon 124 during inflation. Therefore, it may be beneficial to provide a balloon 124 which expands non-uniformly.

According to the exemplary embodiment, electrode 128a is supported by a first portion of balloon 124. The first portion of balloon 124 and a second portion of balloon 124 cooperate to cause balloon 124 to expand in a radially and/or circumferentially non-uniform manner relative to probe 120. Similarly, electrode 128b is supported by a third portion of balloon 124. The first and third portions of balloon 124 cooperate to cause balloon 124 to expand in a radially and/or circumferentially non-uniform manner relative to probe 120. Non-uniform expansion of balloon 124 may cause balloon 124 to substantially contour to the anatomy of a user, for example, to conform to the contours of the user's vagina. Non-uniform expansion of balloon 124 may also facilitate a suitable and comfortable fit of balloon 124 for the user.

According to one embodiment, the second portion may be an expansion portion (e.g., folds, pleats, articulation, etc.), shown as bellows 130. The folds of bellows 130 provide a region of increased surface area of balloon 124 in the deflated state, which allows balloon 124 to expand in a circumferentially non-uniform manner. As shown, bellows 130 extend longitudinally or axially along the tops and bottom of balloon 124. Bellows 130 are further shown to extend around the distal end of balloon 124. Accordingly, bellows 130 are shown to extend substantially continuously around the midsection (e.g. equatorial region) of balloon 124. According to various alternate embodiments, bellows 130 may extend discontinuously, in a left side/right side meridian formation, or in any suitable orientation to cause differential expansion of balloon 124. Probe 120 may include any number of bellows 130 equally or unequally spaced around probe 120. According to the exemplary embodiment, bellows 130 are configured such that a majority of the expansion of balloon 124 occurs in the bellows region. In some embodiments, the bellows 130 include at least two folds extending outward from an interior of the balloon 124. In another embodiment, the bellows 130 include at least three folds extending toward an interior of the balloon 124. In another embodiment, the bellows 130 include at least two folds extending outward from an interior of the balloon 124 and at least three folds extending toward the interior of the balloon 124.

Figure 8:
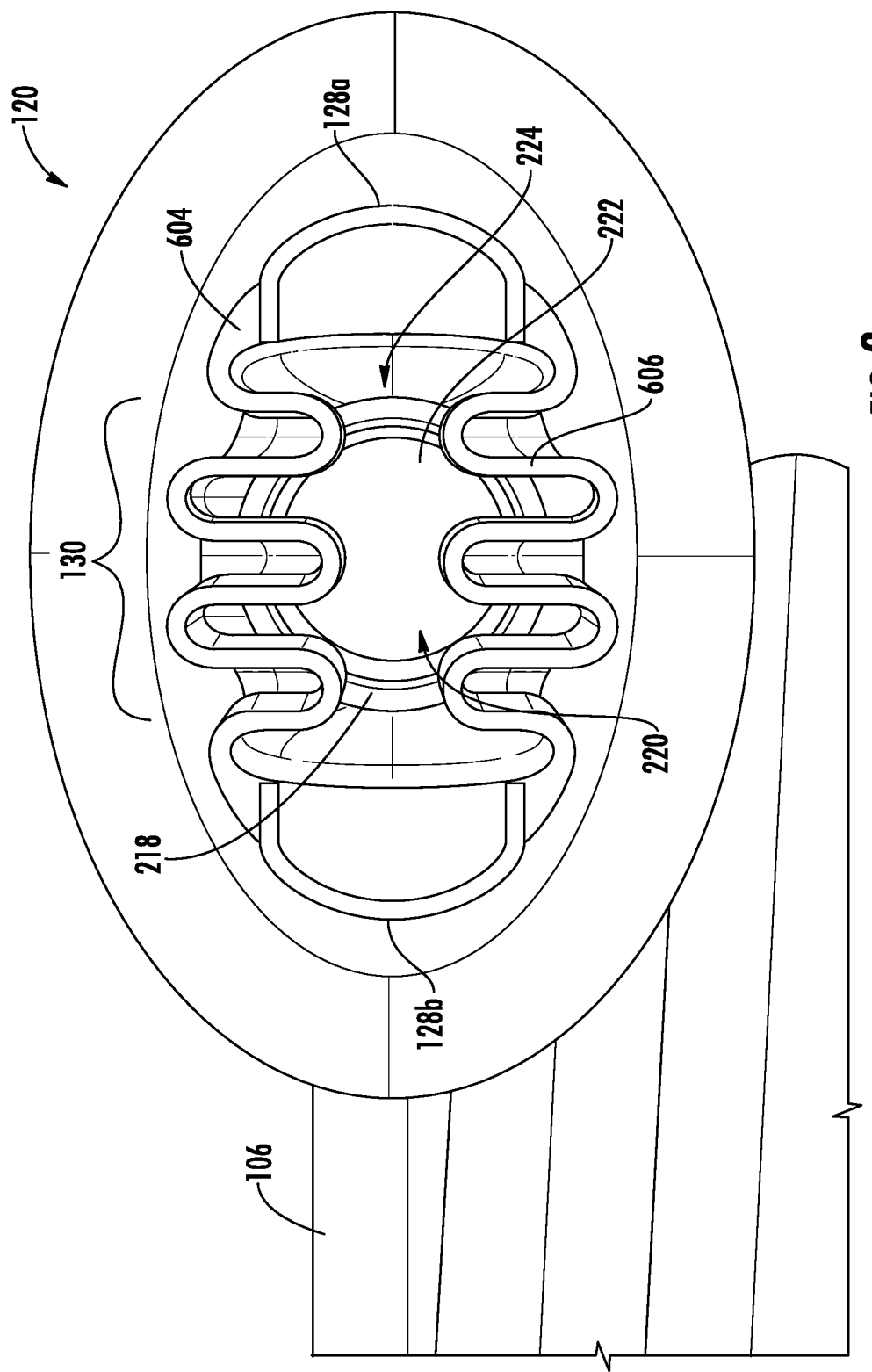
FIG. 8 is a radial cross-section view of the probe of the medical device of FIG. 1, according to an exemplary embodiment.

Referring now to FIG. 8, a radial cross-section view of the probe 120 of the medical device of FIG. 1 is shown according to an exemplary embodiment. As shown, a radial cross-section of probe 120 is shown in a first state (e.g., minimum expansion, contracted, deflated, etc.), while it will be appreciated that probe 120 can also take the form of a second state (e.g., expanded state, inflated, etc.). As seen in the first, deflated state, bellows 130, and the first and third portions of balloon 124 are closely adjacent to one another. However, in the second, or expanded state, bellows 130 have substantially unfolded allowing radial expansion of the first and third portions of balloon 124 and electrodes 128a and 128b provided thereon.

According to another embodiment, the first portion of balloon 124 may have a first thickness 604, and the second portion of balloon 124 may have a second thickness 606, specifically thickness 604 of the first portion being greater than thickness 606 of the second portion. Accordingly, the first portion tends to resist circumferential expansion and maintain its form when balloon 124 is inflated. The second portion provides a "path of least resistance" for expansion, such that for a prescribed level of inflation pressure, balloon 124 will stretch or expand the material of balloon 124 more in the second region than in the first region. The variation in thickness between the first thickness 604 and the second thickness 606 can provide structural support for the balloon 124 in the inflated or deflated states, for example, by preventing the balloon 124 from inflating beyond an expansion or pressure threshold or deflating less than a deflation threshold. In some embodiments, electrodes 128 provide exterior longitudinal structural support of balloon 124 by being integrally formed within the material of balloon 124.

According to one embodiment, at minimum expansion, balloon 124 has a diameter of between approximately 1 inch and approximately 2 inches. In some embodiments, at minimum expansion, balloon 124 has a diameter of approximately 1⅛ inches. According to one embodiment, at maximum expansion, balloon 124 has a diameter of between approximately 2 inches and approximately 4 inches, the preferred maximum expansion of balloon 124 being between approximately 3 inches and approximately 4 inches in diameter. Expansion of balloon 124 in these ranges enables contouring balloon 124 to women of different anatomical sizes.

As discussed above, cavity 224 of probe 120 does not include a structure to support balloon 124. According to the exemplary embodiment, balloon 124 and electrode 228 are configured to provide sufficient rigidity to probe 120 to facilitate insertion of probe 120 into a vagina. In some embodiments, balloon 124 can include a plurality of portions (e.g., members, structures, regions, webs, etc.) configured to support balloon 124. Bellows 130 are sufficiently rigid to inhibit bellows 130 from collapsing into cavity 530. As shown, bellows 130 are configured to maintain balloon 124 in a substantially oval shape when balloon 124 is in a deflated state.

According to the exemplary embodiment seen in FIG. 8, cavity 224 of probe assembly 102 does not include a shaft or other internal structure apart from the balloon 124. As shown, balloon 124 is coupled to handle 110 and interconnected to controller 104 via cable 106.

As shown, probe 120 includes a radially extending flange (e.g., collar), shown as bulkhead 218. Bulkhead 218 is configured to provide a substantially airtight seal between handle 110 and balloon 124. According to the exemplary embodiment, bulkhead 218 includes one or more passages to enable air to fill balloon 124 and to enable electricity to power electrode 128. As shown, passage 220 may is configured to allow a conduit, shown as tube 222 of cable 106, to extend from an inflation device into balloon 124. A substantially airtight seal can be formed (e.g., with silicone glue) between tube 222 and bulkhead 218. A second passage may be configured to allow wires to pass from electrodes 128 and/or other sensors or motors into handle 110. A substantially airtight seal may be formed (e.g., with silicone glue) between any wires and bulkhead 218. Bulkhead 218 may have any number of passages, and the passages may have any orientation on bulkhead 218. Alternatively, bulkhead 218 may include one passage for passing both tube 222 and wires.

Returning to FIG. 1, according to the exemplary embodiment, an electronic control unit, shown as controller 104, is connected to handle 110 via cable 106. In the embodiment shown, controller 104 is a handheld control unit (i.e., one that is sized to fit in the user's hand). Controller 104 includes a power supply 808, processing electronics 800, indicators (e.g., audio, visual, and/or haptic indicators), and control inputs 144 which will be discussed in detail below. According to alternate embodiments, communication between controller 104 and probe assembly 102 may be wireless, for example, using Bluetooth, wireless local area network, or personal area network protocols. According to various other embodiments, any or all of the components of controller 104 may be located on or in probe assembly 102.

Handle 110 may be formed of a plurality of portions, such as a "clam shell" assembly. For example, handle 110 can be made up of various portions that are hollow, substantially symmetric pieces of ABS plastic coupled together to form a housing.

Figure 4:
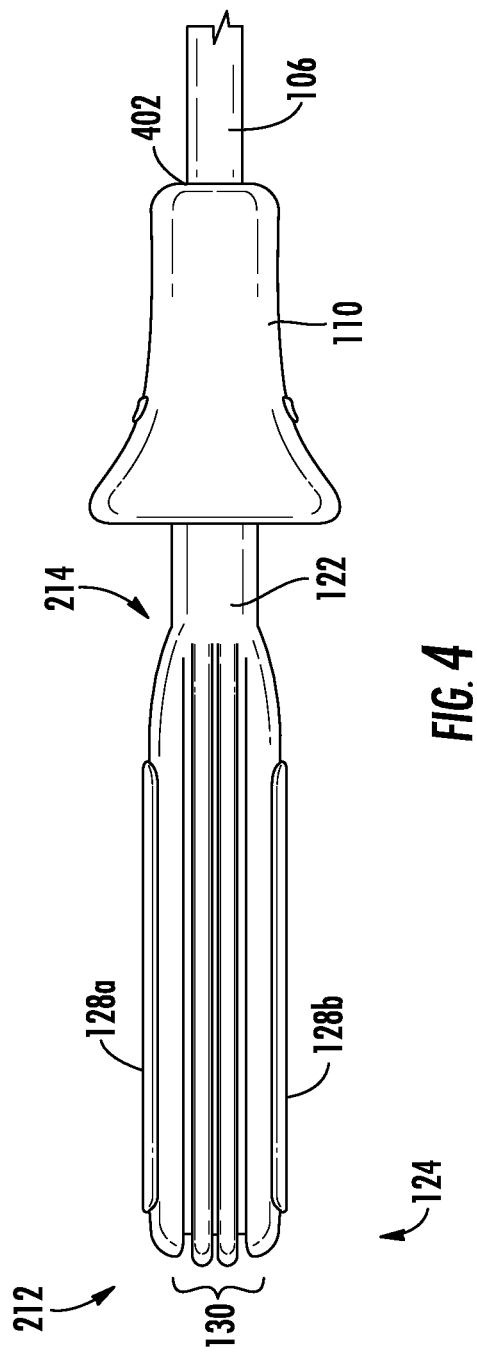
FIG. 4 is a top plan view of the probe of the medical device of FIG. 1, shown according to an exemplary embodiment.
Figure 5:
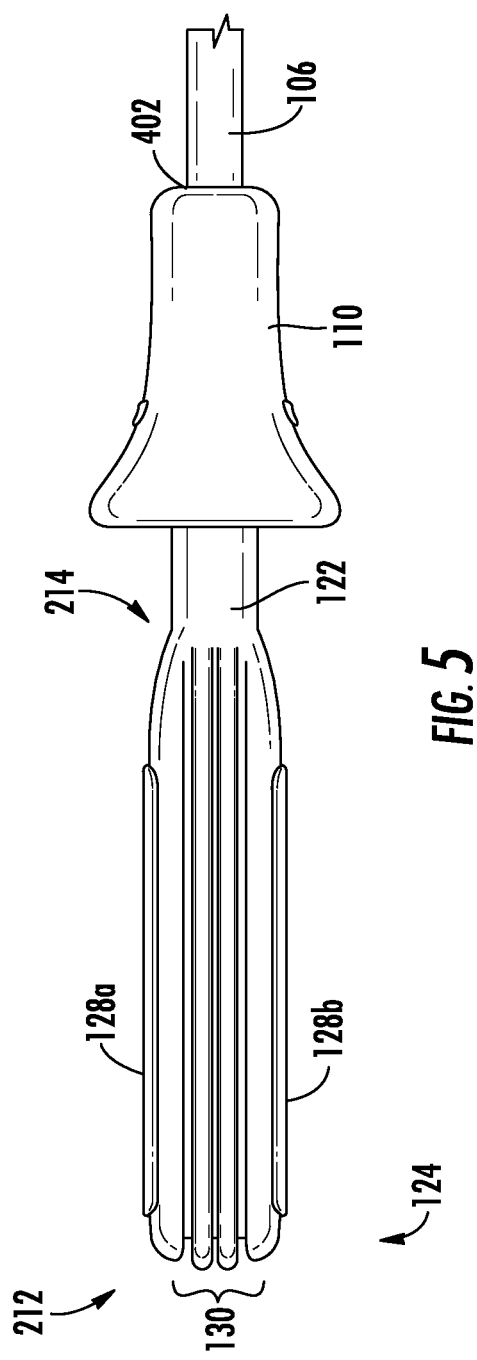
FIG. 5 is a bottom plan view of the probe of the medical device of FIG. 1, shown according to an exemplary embodiment.
Figure 6:
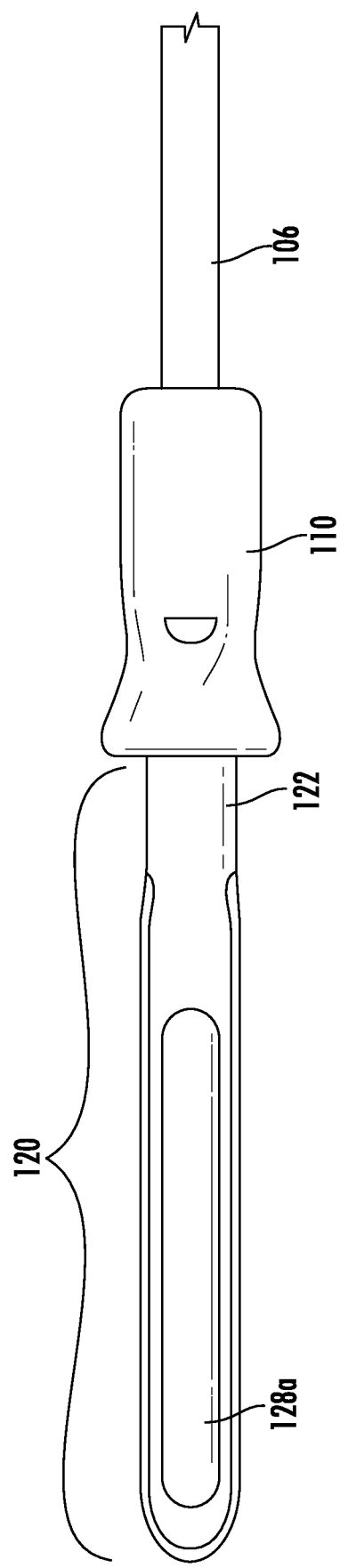
FIG. 6 is a right plan view of the probe of the medical device of FIG. 1, shown according to an exemplary embodiment.
Figure 7:
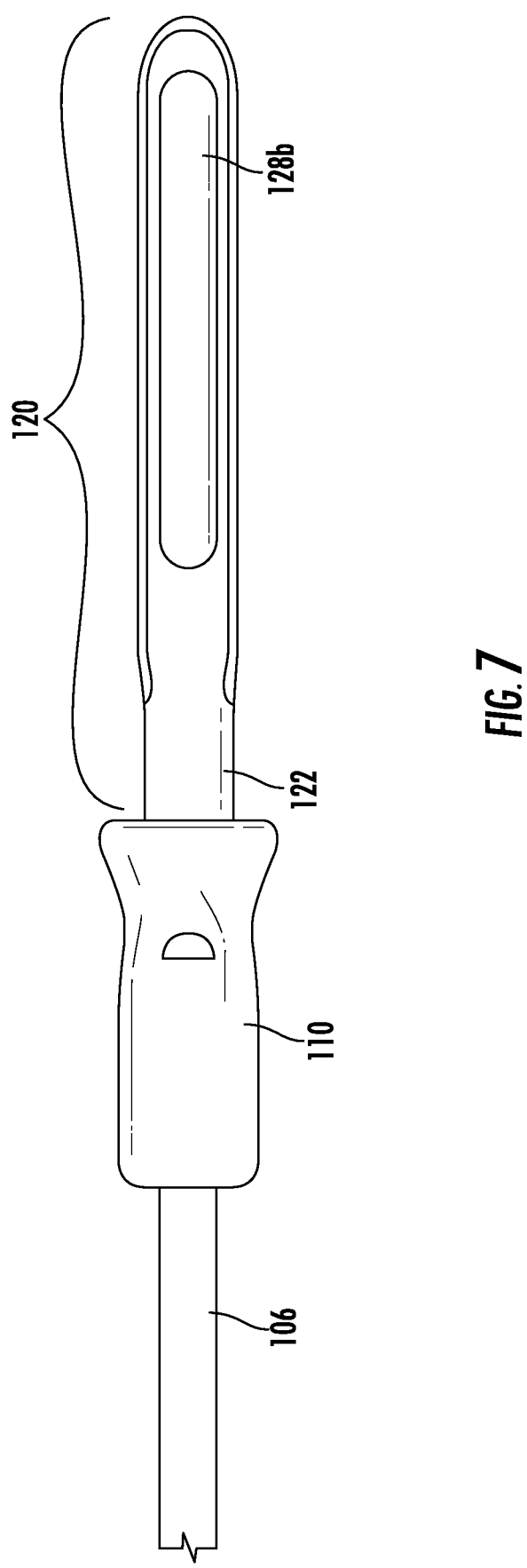
FIG. 7 is a left plan view of the probe of the medical device of FIG. 1, shown according to an exemplary embodiment.

Referring back to FIGS. 4 and 5, top and bottom plan views of the probe assembly 102 of the medical device 100 are shown according to an exemplary embodiment. Handle 110 includes a coupling point 402 configured to receive cable 106. Coupling point 402 may be a jack or orifice in handle 110.

The diameter of balloon 124 may be substantially uniform over the length of probe 120, or the diameter of balloon 124 may vary. As shown, proximal end 214 of balloon 124 has a first diameter, and distal end 212 of balloon 124 has a second diameter, the second diameter being greater than the first diameter. According to one embodiment, probe 120 transitions from the first diameter to the second diameter between neck portion 122 and electrode 128. Varying the diameter of balloon 124 along the length of probe 120 effects the expansion of balloon 124 along the length of probe 120. For example, the smaller proximal diameter limits expansion at proximal end 214 while allowing greater expansion near of balloon 124 near electrodes 128 and distal end 212, thereby contouring balloon 124 to the vaginal cavity. This further enables electrodes 128 to press against vaginal walls without applying excessive pressure on the introitus (vaginal entrance).

In some embodiments, balloon 124 includes a depression, cavity, or pocket configured to receive electrode 128. According to an exemplary embodiment, a periphery of electrode 128 is configured to seat into the pocket, and a sealant (e.g., silicone glue) is used to couple electrode 128 to pocket 402 and to form a substantially airtight seal between electrode 128 and balloon 124. Forming a seal between an outer periphery of electrode 128 and balloon 124 achieves the added benefit of preventing fluid or debris from getting underneath electrode 128, thereby facilitating sanitary maintenance of probe 120.

According to the embodiment shown, probe 120 comprises only one balloon 124. According to various embodiments, probe 120 is in an inserted position when electrodes 128 are located within a vagina. Use of a single balloon has the benefit of minimizing costs (assembly and material) while also simplifying the structure of the device.

Figure 2:
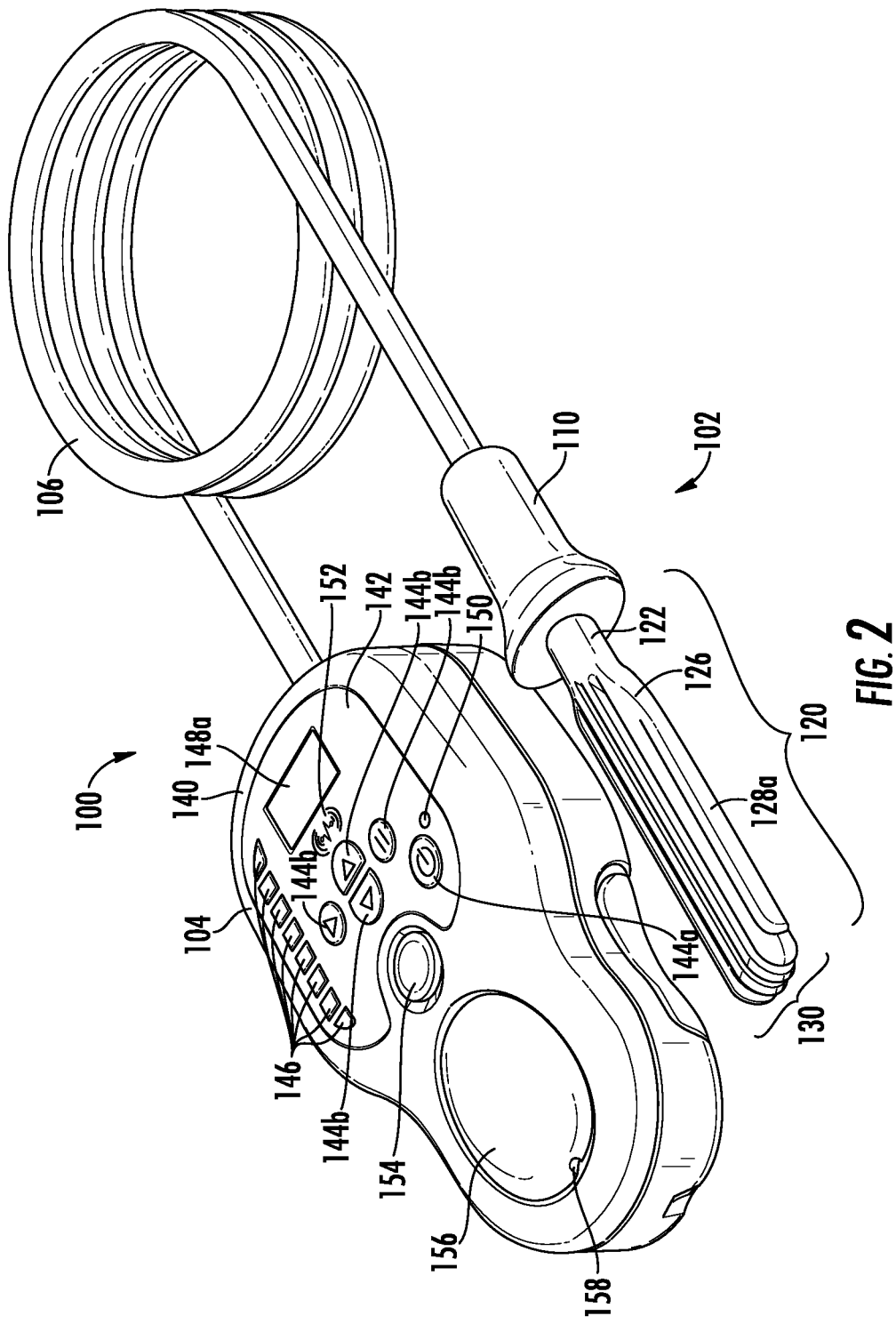
FIG. 2 is a perspective view of another embodiment of the medical device of FIG. 1, shown according to an exemplary embodiment.

Referring again to FIGS. 1 and 2, perspective views of controller 104 are shown according to the exemplary embodiments of FIGS. 1 and 2. As shown, controller 104 may include a housing 140, a front panel 142, and a cavity that receives one or more batteries to supply power to device 100. Front panel 142 may include a plurality of control inputs (e.g., toggles, switches, an electro-acoustic transducer configured to receive voice commands, a touch sensitive display, etc.), shown as control inputs 144 (e.g. buttons), configured to enable user input into controller 104. For example, control inputs 144a may be a power button configured to turn controller 104 on and off. Control inputs 144a may be a combination power/mode button configured to turn controller 104 on and off and to switch between operating states. According to an exemplary embodiment, control inputs 144b may provide other control inputs, for example, stimulation select, pressure select, increase, decrease, pause, etc.

According to the embodiment shown, front panel 142 includes a plurality of sequentially oriented lamps 146 (e.g., lights, LEDs, etc.) configured to indicate the level of stimulation intensity and/or pressure inside balloon 124. Controller 104 may also include a display 148, shown as display 148a and display 148b, configured to numerically indicate balloon pressure and/or stimulation intensity. Display 148 may be further configured to display videos, for example instructional videos, or to display a waveform representative of the stimulation signal. Display 148 and the plurality of lamps 146 may indicate the same or different information. Front panel 142 may include an indicator lamp 150 (e.g. lights, LEDs, etc.) which may indicate a power state (e.g., power on, battery low, etc.), a communication state (e.g., communication to a computer, to probe assembly 102, etc.), pressure state (e.g., the pressure inside balloon 124 has reached a predetermined value), an error state, etc. According to an alternate embodiment, controller 104 may include a touchscreen configured to both provide information to a user and to receive input from a user. Using a touchscreen would provide an easy to clean surface, thereby facilitating sanitary hygiene. As shown in FIG. 1, in embodiments having a touchscreen display 148b, the functionalities of control inputs 144 can be implemented using touchscreen display 148b and therefore various control inputs 144 (e.g., buttons) are not required. Controller 104 can also include a stimulation indicator, shown as active stimulation LED indicator 152. Active stimulation LED indicator 152 can illuminate as stimulation is being delivered via electrode 128, upon which the user can use to either increase or decrease electric stimulation using control inputs 144b to identify the level of electric stimulation that activates a comfortable full muscle contraction.

Controller 104 may also include an audio device 714 that may be configured to provide motivation and/or audio instruction to a user. According to one embodiment, the audio device 714 may announce that the pressure inside balloon 124 has reached a prescribed level. According to another embodiment, the audio device 714 may request a user to force a contraction of the muscle in communication with electrodes 128.

Controller 104 may include an inflation device. A portion of controller 104 can be formed of a deformable material, for example, a silicone rubber covering the inflation device and which is sufficiently pliable to compress the inflation device and to return to shape. The deformable material may be formed of the same or different materials than the rest of controller 104, or may be formed as one element with controller 104. Controller 104 is further shown to include a release valve 154, discussed in detail below.

The inflation device can be located at least partially in a top part of controller 104 and configured to selectively inflate and deflate balloon 124. According to an exemplary embodiment, the inflation device includes a pump 156 which may be manually operated by, for example, pressing and depressing the deformable material. Pump 156 includes a cavity (e.g., a bladder) and a check valve that permits air to enter the bladder through air inlet 158 from outside of the controller 104 and probe assembly 102, and prevents air from exiting back through air inlet 158 when the bladder is compressed by a user pressing on the pump 156. Additional check valves may be utilized (e.g., a second check valve located between balloon 124 and the bladder) to permit air to enter balloon 124 from the bladder and to prevent air from back flowing into the bladder 512, for example, when the bladder expands.

In some embodiments, a tee connector couples the bladder, release valve 154, and cable 106. The release valve may be of any suitable mechanism to permit air under pressure to be selectively released from balloon 124, for example a thumbscrew or a pushbutton. The release valve may also act as a relief valve to prevent over-pressurization of balloon 124. For example, a tube internal to cable 106 extends from an outlet of the tee connector into balloon 124 of probe 120. In operation, squeezing the inflation device compresses the bladder and forces air through the tee connector and the tube of cable 106 into balloon 124. When the squeezing force exerted on the bladder is released, the bladder will resume its natural, inflated position as air is drawn into the bladder through the check valve and air inlet 158. The bladder is squeezed and released repeatedly to force pressurized air into balloon 124. Increased pressure in balloon 124 eventually causes inflation of balloon 124, which in turn causes electrode 128 to contact a vaginal wall. According to one embodiment, the level of inflation of balloon 124 is controlled by a user and may be selected to ensure a suitable and comfortable fit between balloon 124 and the user's vagina. According to another embodiment, the appropriate level of inflation is communicated to the user by a health care professional. According to another embodiment, the appropriate level of inflation is stored in memory 920 of processing electronics 800 described below. According to various alternate embodiments, the inflation device may include a motorized pump, the inflation device may be located in handle 110 and pressurized air directed into balloon 124 without passing through cable 106, and/or the inflation device may be located within probe 120. As described, the pressurizing fluid of the exemplary embodiment is air; however, any suitable pressurizing fluid may be used, for example, water, saline, oil, or other gases or liquids.

According to an exemplary embodiment, device 100 may include a pressure sensor 804 located in probe assembly 102 or controller 104 and barometrically connected to balloon 124. According to one embodiment, a sampling tube extends from the interior of balloon 124 to the pressure sensor 804. According to other embodiments, a sampling tube may extend from cable 106 or the tee connector to the pressure sensor 804. According to other embodiments, the pressure sensor 804 may be located in-line with the tube of cable 106, located in probe 120, for example in cavity 224, or located in controller 104. The pressure sensor 804 may visually display an indication of pressure on controller 104 or handle 110, for example, a gauge, a light, a digital display, etc. According to an exemplary embodiment, the pressure sensor 804 is configured to communicate (via wires or wirelessly) pressure information to processing electronics 800. For example, the pressure sensor 804 may generate a response information, e.g., a signal indicative of the contractive force of the muscles on balloon 124. The response information may correlate to a rise in pressure created in balloon 124 by the contracting muscle acting on balloon 124. The response information may be triggered by the electrical stimulation provided by electrodes 128 or may be triggered by the user manually (e.g., consciously, volitionally, voluntarily, etc.) forcing a contraction of her pelvic floor muscles.

Cable 106 is configured to couple to controller 104 using a connector. According to an exemplary embodiment, the connector is a D-sub-9 connector. According to alternate embodiments, any suitable connector may be used (e.g., a Universal Serial Bus connector). Cable 106 may be decoupled from controller 104, and controller 104 may then be coupled to a computer to receive firmware (e.g., configuration data) or protocol data updates from the computer. According to various alternate embodiments, controller 104 may wirelessly connect to a computer, controller 104 may include an interface which enables the protocol to be entered directly into controller 104, or cable 106 is configured to remain coupled to controller 104 and to de-couple from probe assembly 102.

Operation of device 100 is described below according to an exemplary embodiment. A method for treating urinary incontinence in a female includes inserting probe 120 into the vagina, pressurizing balloon 124 to inflate balloon 124 such that electrodes 128 contact the walls of the vagina (e.g., to place electrodes 128 snugly against the walls of the vagina to provide an electrical conduction pathway from the electrodes to the muscles and/or associated nerves), and periodically supplying a pulsed electrical stimulation to electrodes 128 to stimulate the muscles. In this manner, balloon 124 allows device 100 to ensure a proper fit with differing anatomies. As the muscles contract in response to the electrical stimulation, the muscle walls of the vagina exert a force on inflated balloon 124, and as the muscles contract, balloon 124 is compressed. Pressure sensor 804 generates a signal indicative of the contractive force of the muscles on balloon 124 triggered by the electrical stimulation provided through the electrodes 128. The signal from pressure sensor 804 may be communicated (e.g., via wired or wireless connections) to processing electronics 800. Processing electronics 800 may be configured to process the signal from pressure sensor 804 to determine information related to muscle contraction caused by the electrical stimulation (e.g., the force or strength of muscle contraction, the duration of muscle contraction, etc.). When muscle contraction stops, the air pressure within balloon 124 causes balloon 124 to expand to an original inflated size. The method also includes using a biphasic pulse. The progress of the treatment can be monitored by evaluating the increase in strength of muscle activity by measuring muscle contraction over a number of treatment sessions. Urinary incontinence in general, and urinary incontinence in females specifically, may be treated by strengthening the muscles that are responsible for bladder control (e.g., the pelvic floor muscles) using internal electrical stimulation. This treatment may be useful for women who have become incontinent with age or women who have become incontinent due to recent childbirth. According to one embodiment, device 100 may be used three weeks after childbirth.

According to the exemplary embodiment described, processing electronics 800 supply a biphasic pulse of electrical current to electrodes 128 which in turn stimulates contraction of the muscles. For example, the biphasic pulse may have a first stimulation phase providing a pulse at 12 hertz for 6 seconds followed by a first rest period having a duration of 6 seconds. A second stimulation phase providing a pulse at 25 hertz for six seconds follows the first rest period, and a second rest period having a duration of 6 seconds follows the second phase. The use of a biphasic pulse (e.g., a pulse having two stimulation periods having different frequencies) prevents the muscles from becoming adjusted or de-sensitized to the electrical stimulation. This sequence of stimulation phases and rest phases repeats for a treatment period as necessary. A typical treatment period is approximately 15 minutes. In another embodiment, a multiphasic pulse (e.g., a plurality of different pulse durations and/or frequency between pulses) may be used. Within each stimulation phase, a symmetric alternating current may be applied to the muscle via electrodes 128 to reduce the effects of electrophoresis or cataphoresis on the muscle tissues. For example, applying a current of a positive first value for a first pulsewidth (e.g., 200 microseconds), applying no current for 40 microseconds, and then applying a current of a negative first value for a first value (e.g., 200 microseconds) limits the migration of ions with the muscle tissue. This pattern of alternating current pulsewidths may then be repeated at various frequencies (hertz), e.g., 12 hertz, 25 hertz, 50 hertz, etc. Accordingly, the amount of time between the end of the negative current until the beginning of the positive current depends on the frequency. Placing a short rest period (e.g., 40 microseconds) between the bipolar phases may improve circuit reliability.

In other embodiments, other frequencies and/or durations for the stimulation phases and/or rest periods may be used. For example, in one embodiment, the frequency delivered may be variable, and frequencies up to 50 hertz may be delivered. The current delivered during the stimulation phase may be substantially between 10 milliamps and 50 milliamps. According to another embodiment, electronics 800 supply a biphasic pulse of electrical potential between electrodes 128. The electrical potential between electrodes 128 may be substantially between 10 Volts and 50 Volts. It is believed that these ranges of current and voltage provide therapeutic benefit. According to another embodiment, stimulation may occur as low as 4-5 Volts. Contraction of the muscle is a function of current (or voltage) amplitude, pulsewidth, and frequency applied to the muscle. Further, the rate at which the muscle relaxes has a minimum persistence time that is affected by the strength and duration of the contraction. If the period (i.e., 1/frequency) of stimulation is greater than the minimum persistence time of the contraction, a user may perceive the stimulation as convulsions rather than a continuous contraction. Accordingly, processing electronics 800 may be configured to control one of frequency, pulsewidth, and amplitude in order to maintain a contraction perceived by the user as substantially continuous. According to one embodiment, processing electronics 800 may be configured to control one of frequency, pulsewidth, and amplitude based on the other two in order to maintain a substantially continuous contraction. Additionally, processing electronics 800 may be configured to ramp at least one of frequency, amplitude, and pulsewidth at the beginning and/or end of each phase. Ramping the frequency, amplitude, and/or pulsewidth may reduce the step function of stimulation entering a phase, which may be uncomfortable or startling for some users. According to one embodiment, the pulsewidth may be stepped up by a fraction of the desired pulsewidth (e.g., 50 microseconds) per cycle until the desired pulsewidth (e.g., 200 microseconds) is reached. Processing electronics 800 may inhibit certain combinations of frequency, current, and voltage. According to the exemplary embodiment described, a health care professional may cause the stimulation parameters to be stored in processing electronics 800. In various alternate embodiments, the user, via an control inputs 144 located on the controller 104, may control the frequency of the electrical signal being supplied, may control the current delivered during each stimulation phase, or may control the voltage delivered during each stimulation phase.

According to an exemplary embodiment, protocol data 926 (e.g., prescribed pressure, prescribed stimulation frequency, amplitude, pattern, etc.) may be stored into memory 920 in controller 104 by a non-user of probe 120 (e.g., a healthcare professional). Controller 104 and probe assembly 102 may then be provided to the probe user (e.g., a patient); however, the probe assembly user cannot change the protocol. According to alternate embodiments, the probe user may change the protocol, or the probe user may download a healthcare professional prescribed protocol into memory 920 of controller 104.

Figure 9:
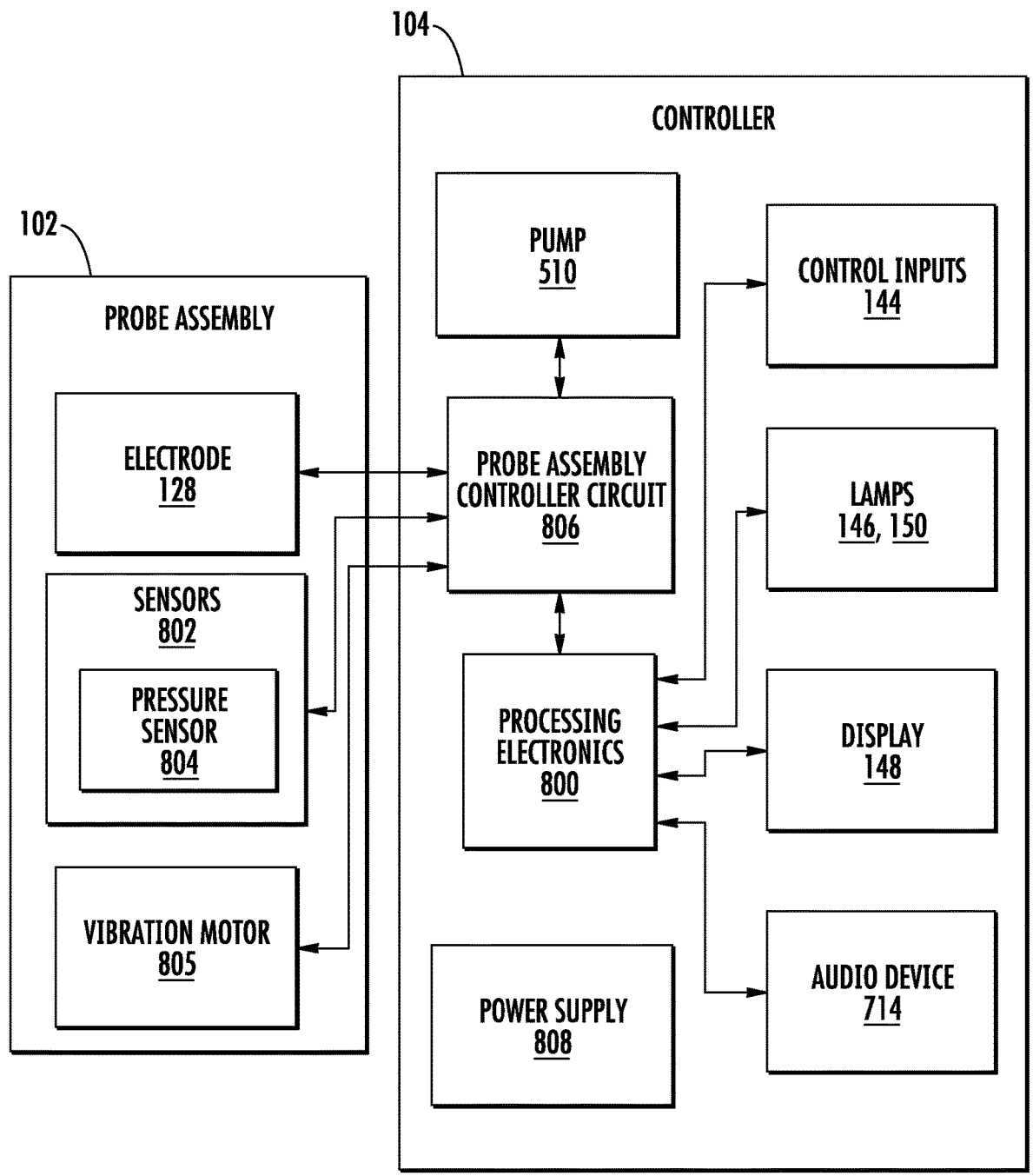
FIG. 9 is a schematic block diagram of the medical device of FIG. 1, shown according to an exemplary embodiment.

Referring to FIG. 9, a block diagram of device 100 is shown according to an exemplary embodiment. Probe assembly 102 is shown to include an electrode 128 and sensors 802, including pressure sensor 804, and vibration motor 805. First electrode 128a and/or second electrode 128b are configured to provide an electrical signal (e.g., current, voltage, frequency, etc.) to a muscle in communication with the electrode. According to various embodiments, probe assembly 102 may have one or a plurality of electrodes. Probe assembly 102 may include one or more sensors 802 (e.g., a capacitive sensor, pressure sensor 804, a conductivity sensor, etc.). Sensors 802 may be disposed in any suitable location in probe assembly 102 (e.g., in handle 110, in cavity 224, etc.). Vibration motors 805 may be configured to provide haptic feedback to a user in response to user input through an control inputs 144 or as an indication that balloon 124 has been inflated to a predetermined pressure. Alternatively, vibration motor 805 for may be located in cavity 224 and configured to provide a pleasurable sensation to a user. The pleasurable sensation may induce a user to maintain compliance with a prescribed treatment regimen. The pleasurable sensation may be used to cause an orgasm, which in turn causes a release of serotonin and norepinephrine in the user which may improve the user's mood and treat depression, specifically post-partum depression.

According to an exemplary embodiment, controller 104 includes control inputs 144, lamps 146, 150, display 148, pump 156, audio device 714, processing electronics 800, probe assembly controller circuit 806, and power supply 808. The control inputs may include any suitable user interface, e.g., control inputs 144 (e.g., buttons), toggles, switches, an electro-acoustic transducer configured to receive voice commands, a touch sensitive display, etc. Lamps such as lamps 146, 150 may provide information to a user through illumination, brightness, color, blinking pattern, and/or illumination of a subset of a plurality of spatially oriented lamps.

Display 148 may also be configured to provide alphanumeric or graphical images. For example, after insertion and powering on of the probe assembly 102, display 148 can be configured to display a "Begin Inflating" indicator that then transitions to an inflatable probe pressure range bar indicator. The inflatable probe pressure range bar indicator can provide a range of ideal pressure for the balloon 124 to inflate. In another example, during a stimulation session, when inputs are made using display 148b or input control 144b to increase or decrease a stimulation level, a stimulation indicator will illuminate as stimulation is being delivered that corresponds to the stimulation level. In another example, during a biofeedback session, display 148 can be configured to display visual cues (e.g., a squeeze indicator, or a relax indicator) and a timer indicating how long the user is to contract and relax their pelvic floor muscles, and a force indicator representing a contraction force of the pelvic floor muscles of the user.

Pump 510 is configured to cause inflation of balloon 124 and may be manually operated or motorized. Audio device 714 may be a speaker configured to provide aural information to a user and may be combined with or separate from the electro-acoustic transducer control input. Probe assembly controller circuit 806 is shown coupled to probe assembly 102 and may include any number of mechanical or electrical circuitry components or modules for a pump 156, electrode 128, sensors 802, and/or vibration motors 805 of probe assembly 102. For example, circuit 806 may be configured to send electrical signals to pelvic floor muscles while sending response information to processing electronics 800.

Controller 104 is further shown to include a power supply 808. Power supply 808 is configured to provide electrical power to device 100 and components thereof. According to an exemplary embodiment, device 100 is configured to be powered by a 6 Volt battery. According to other embodiments, device 100 may use other voltages, a rechargeable battery, or may be plugged into utility power supply. Power supply 808 or processing electronics 800 may be configured to increase the voltage and/or amperage available to electrodes 128, for example, up to 110V. According to one embodiment, the maximum electrical potential generated between the first electrode 128a and second electrode 128b is approximately 80 Volts. According to another embodiment, it is believed that the maximum therapeutic range of the electrical potential generated between first electrode 128a and second electrode 128b is approximately 50 Volts.

While the exemplary embodiment shows a separate probe assembly 102 and controller 104, it is contemplated that any or all of the components shown as part of controller 104 may be located in probe assembly 102. For example, lamps 146 and/or lamps 150 may be located on handle 110. Alternatively, control inputs 144, lamps 146, 150, display 148, audio device 714, processing electronics 800, and probe assembly controller circuit 806 may be located in handle 110. According to another embodiment, pump 156 is located in controller 104.

Figure 10:
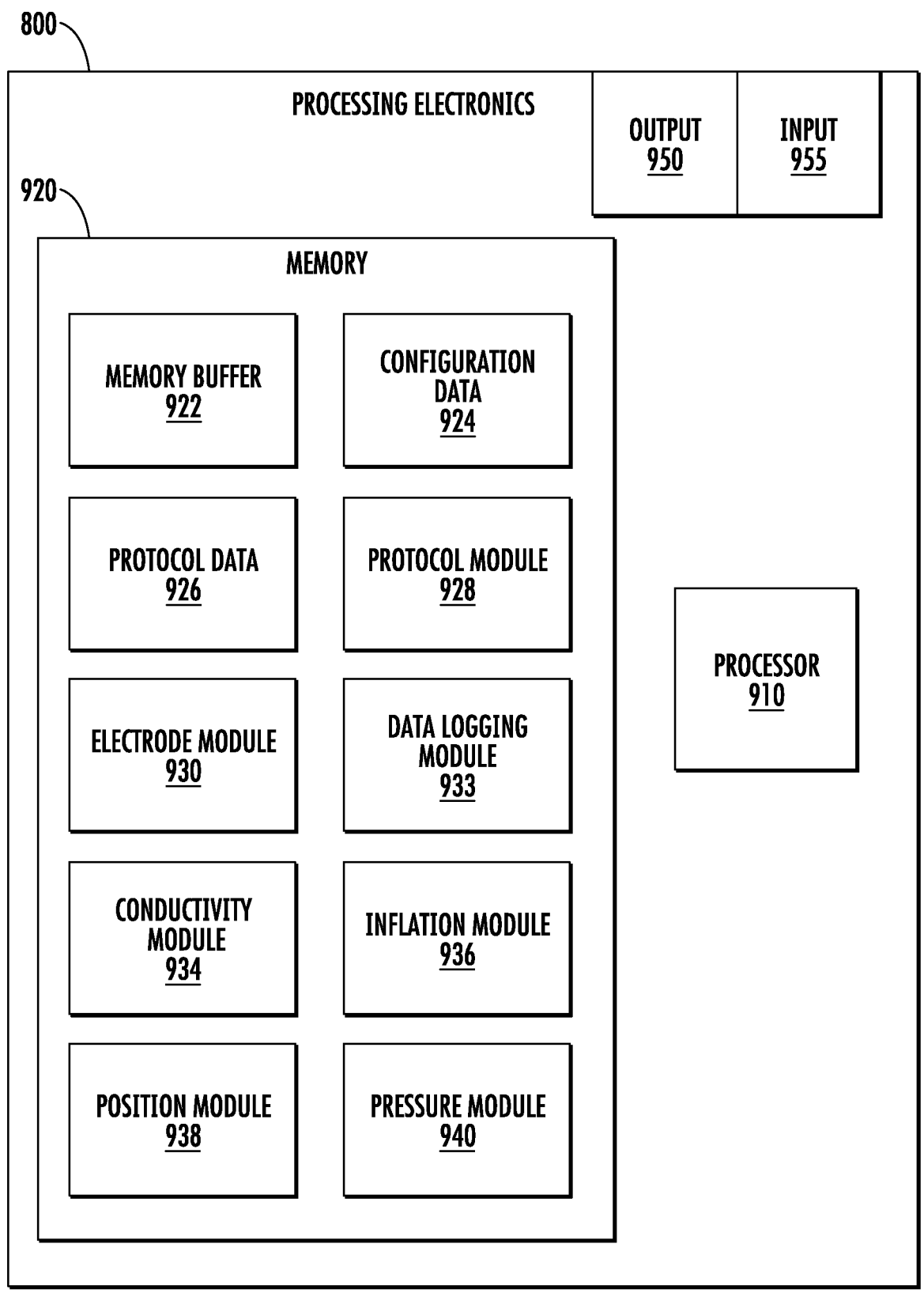
FIG. 10 is a schematic block diagram of processing electronics of the medical device of FIG. 1, shown according to an exemplary embodiment.

Referring to FIG. 10, a detailed block diagram of processing electronics 800 of FIG. 9 is shown, according to an exemplary embodiment. Processing electronics 800 includes a processor 910 and a memory 920. According to an exemplary embodiment, processor 910 is configured to execute computer code stored in memory 920 to complete and facilitate the activities described herein. For example, memory 920 is shown to include modules 922-940 which are computer code modules (e.g., executable code, object code, source code, script code, machine code, etc.) configured for execution by processor 910. When executed by processor 910, processing electronics 800 is configured to complete the activities described herein. Processing electronics includes hardware circuitry for supporting the execution of the computer code of modules 922-940. For example, processing electronics 800 includes hardware interfaces (e.g., output 950) for communicating control signals (e.g., analog, digital) from processing electronics 800 to circuit 806. Processing electronics 800 may also include an input 955 for receiving, for example, sensor data from circuit 806, response information from circuit 806, user inputs from control inputs 144, or for receiving data or signals from other systems or devices. According to various embodiments, processor 910 may be or include one or more microprocessors, an application specific integrated circuit (ASIC), a circuit containing one or more processing components, a group of distributed processing components, circuitry for supporting a microprocessor, or other hardware configured for processing. Memory 920 can be any volatile or non-volatile memory device capable of storing data or computer code relating to the activities described herein.

Memory 920 includes a memory buffer 922 for receiving sensor data, for example response information, pressure data, voltage data, capacitive sensing data, conductivity data, etc. The sensor data may be stored in memory buffer 922 until buffer 922 is accessed for data. For example, a protocol module 928, electrode module 930, data logging module 932, conductivity module 934, inflation module 936, position module 938, pressure module 940, or another process that uses sensor data may access buffer 922. The sensor data stored in memory 920 may be stored according to a variety of schemes or formats. For example, the sensor data may be stored as streaming data, peak values, synchronous, asynchronous, separate buffers for each data type, one buffer for all sensor data, or any other suitable format for storing sensor information.

Memory 920 further includes configuration data 924. Configuration data 924 includes data relating to device 100, such as electrode information that the electrode module 930 can interpret to determine how to command the electrodes 128 to cause a muscle contraction, for example the number of electrodes, electrode conductivity, conductivity as a function of expansion or pressure, etc. According to another embodiment, configuration data 924 may include response information configuration data which the protocol module 928 and/or data logging module 932 can interpret to determine if response information will include an electrical signal received from at least one of the electrodes 128, a pressure signal received from a pressure sensor 804, or both. According to another embodiment, configuration data 924 may include pump information, such as whether the pump 156 is hand-operated or motorized, and control information of the motorized pump. According to another embodiment, configuration data 924 may include sensor information, such as the existence, location, and calibration of pressure sensors 804, conductivity sensors, capacitive sensors, and the like.

Memory 920 further includes a protocol data 926 which includes data relating to the treatment protocol. Protocol data 926 may include data that protocol module 928 can interpret to determine how to command the electrical signal sent to electrodes 128. For example, protocol data 926 may include data relating to current, voltage, frequency, number of phases of stimulation signal, duration and pattern of stimulation periods, duration and pattern of rest periods, and/or duration of treatment. Protocol data 926 may include data relating to a predetermined pressure (e.g., prescribed pressure, target pressure, threshold pressure, etc.) for balloon 124. Protocol data 926 may be stored in memory 920 by the user or another (e.g., a health care professional).

Memory 920 further includes a protocol module 928 which includes logic for using configuration data 924, protocol data 926, sensor data from the memory buffer 922, and/or data received from another module to carry out the treatment protocol, e.g., providing stimulation commands to electrode module 930. Protocol module 928 may output data to data logging module 932 for recording, may cause outputs for providing an indication to a user, and may cause an output requesting a user to perform an activity (e.g., inserting probe 120, pressurizing balloon 124, forcing a contraction, etc.). Protocol module 928 may include logic to cause closed-loop control of the electrical stimulation based on response information received from memory buffer 922, electrode module 930, conductivity module 934, and/or pressure module 940.

Memory 920 further includes an electrode module 930 which includes logic for causing a contraction of a muscle in communication with electrode 128. Electrode module 930 may control the stimulation of a muscle in communication with electrodes 128 based on conductivity information received from conductivity module 934, position information received from position module 938, and/or pressure information received from pressure module 940. Electrode module 930 may include logic to control the current or voltage provided by electrodes 128 as a function of frequency, or to control the frequency in response to the current or voltage. According to an exemplary embodiment, electrode module 930 may include logic to use an 8-bit register to control the frequency, current, or voltage of the stimulation. Using an 8-bit register provides fine resolution for precise incontinence treatment.

Memory 920 further includes a data logging module 932 which includes logic for causing a response information to be recorded. Data logging module 932 may include logic for storing baseline information. Data logging module 932 may record processed information or may record raw sensor information, may record data directly from protocol module 928, may record data from memory buffer 922 or another module, and/or may record frequency and duration of use information. Recording frequency and duration of use information may provide a record of whether a patient is adhering to a protocol and complying with a daily usage and time regimen.

Memory 920 is shown to include a conductivity module 934 which includes logic for determining the conductivity of the environment of probe 120, balloon 124, and/or electrodes 128. Conductivity of the environment is dependent on many factors. For example, conductivity may depend on the conductivity and quantity of artificial lubricants used, the quantity of vaginal fluid present, which may change from day to day or during the treatment protocol, and/or the expansion of electrodes 128. Conductivity module 934 may receive sensor data directly or through memory buffer 922. Conductivity module 934 may provide conductivity information to electrode module 930, data logging module 932, or any other module requiring conductivity information.

Memory 920 is shown to include an inflation module 936 which includes logic for providing an indication to a user that the pressure inside balloon 124 has reached a predetermined value. According to one embodiment, the predetermined value is a pressure stored in protocol data 926. Inflation module 936 may use sensor data from memory buffer 922 or pressure information from pressure module 940. Inflation module 936 may include logic for causing inflation of balloon 124. For example, inflation module 936 may cause a request for a user to actuate pump 156 or may cause actuation of a motorized pump 156. Inflation module 936 may control pump 156 using configuration data 924 and pressure data received from memory buffer 922 or pressure module 940.

Memory 920 is shown to include a position module 938 which includes logic for determining if probe 120 is inserted and/or properly positioned. According to one embodiment, position module 938 may receive capacitive sensor data from memory buffer 922. According to an alternative embodiment, position module 938 may determine insertion of probe 120 from a change in continuity or a change in resistance between electrodes 128. According to another alternative embodiment, position module 938 may request user confirmation that probe 120 and/or balloon 124 are inserted, for example, by providing input via control inputs 144 on controller 104. Position module 938 may cause output from electrode module 930 to be inhibited if position module 938 determines that balloon 124 has been removed from the vagina. For example, position module 938 may cause electrodes 128 to stop providing an electric signal, or position module 938 may provide position information to protocol module 928 or to electrode module 930.

Memory 920 further includes a pressure module 940 which includes logic for determining the pressure inside balloon 124. Pressure module 940 may use configuration data 924, pressure data received directly from pressure sensor 804, or pressure data received from memory buffer 922. Pressure module 940 may provide pressure information to inflation module 936 and protocol module 928. Pressure module 940 may provide pressure information to electrode module 930, or may inhibit processing electronics 800 from causing a contraction of the muscle if the pressure in balloon 124 is below a threshold value, e.g., balloon 124 has not been sufficiently inflated. Pressure module 940 may receive response information from pressure sensor 804.

Figure 11:
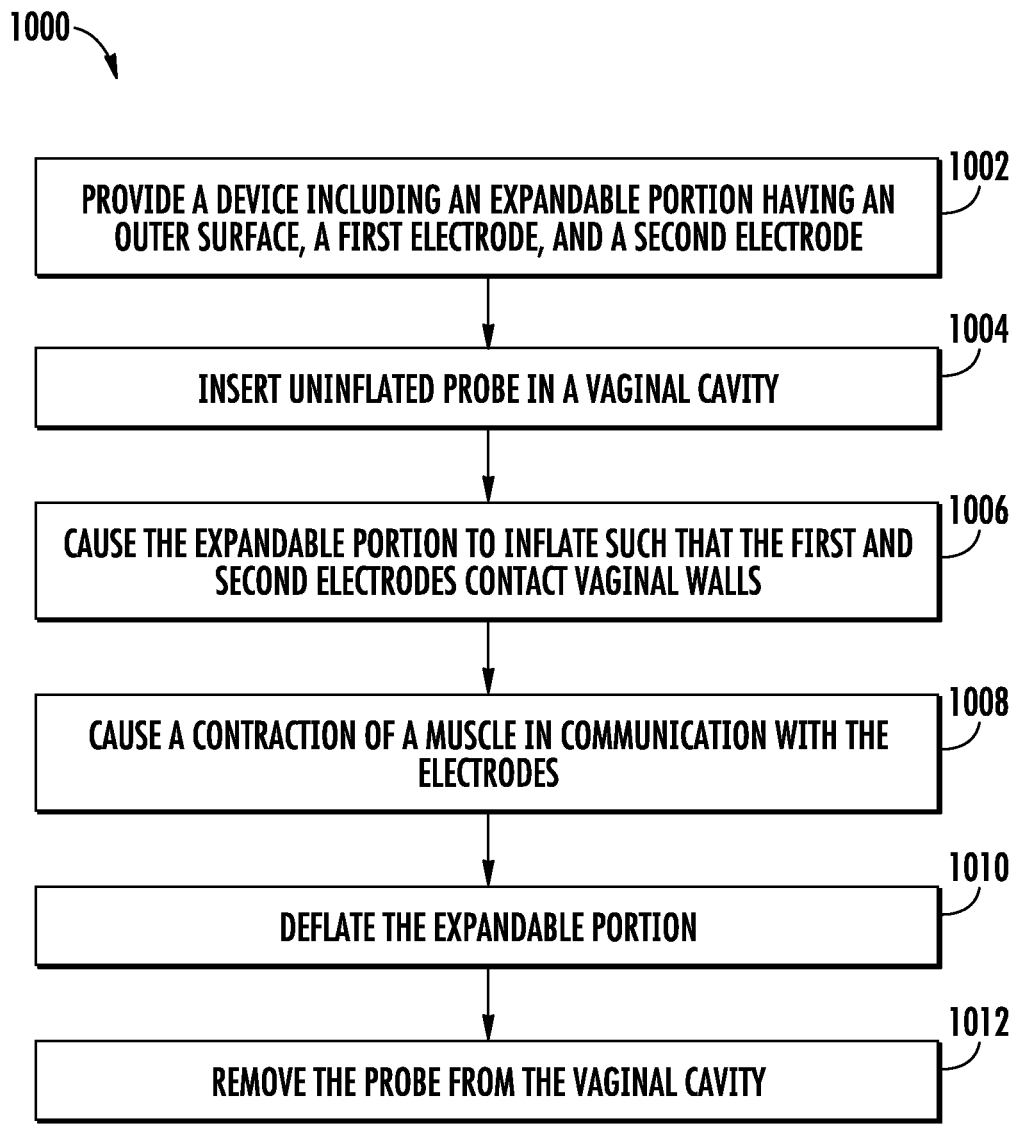
FIG. 11 is a schematic flow chart of a process for treating urinary incontinence using the medical device of FIG. 1, shown according to an exemplary embodiment.

Referring to FIG. 11, a flowchart of a process 1000 for treating urinary incontinence is shown according to an exemplary embodiment. Process 1000 is shown to include the steps of providing a device as described above and including an expandable portion having an outer surface, a first electrode, and a second electrode (step 1002). Process 1000 further includes the steps of inserting the uninflated probe in a vaginal cavity (step 1004), causing the expandable portion to inflate such that the first and second electrodes contact vaginal walls (step 1006), and causing a contraction of the muscle in communication with the electrodes (step 1008). Process 1000 further includes deflating the expandable portion (step 1010) and removing the probe from the vaginal cavity (step 1012). According to one embodiment, the first and second electrodes couple to the outer surface of the expandable portion and are configured to cause a contraction of a muscle and communication with the electrodes.

Figure 12:
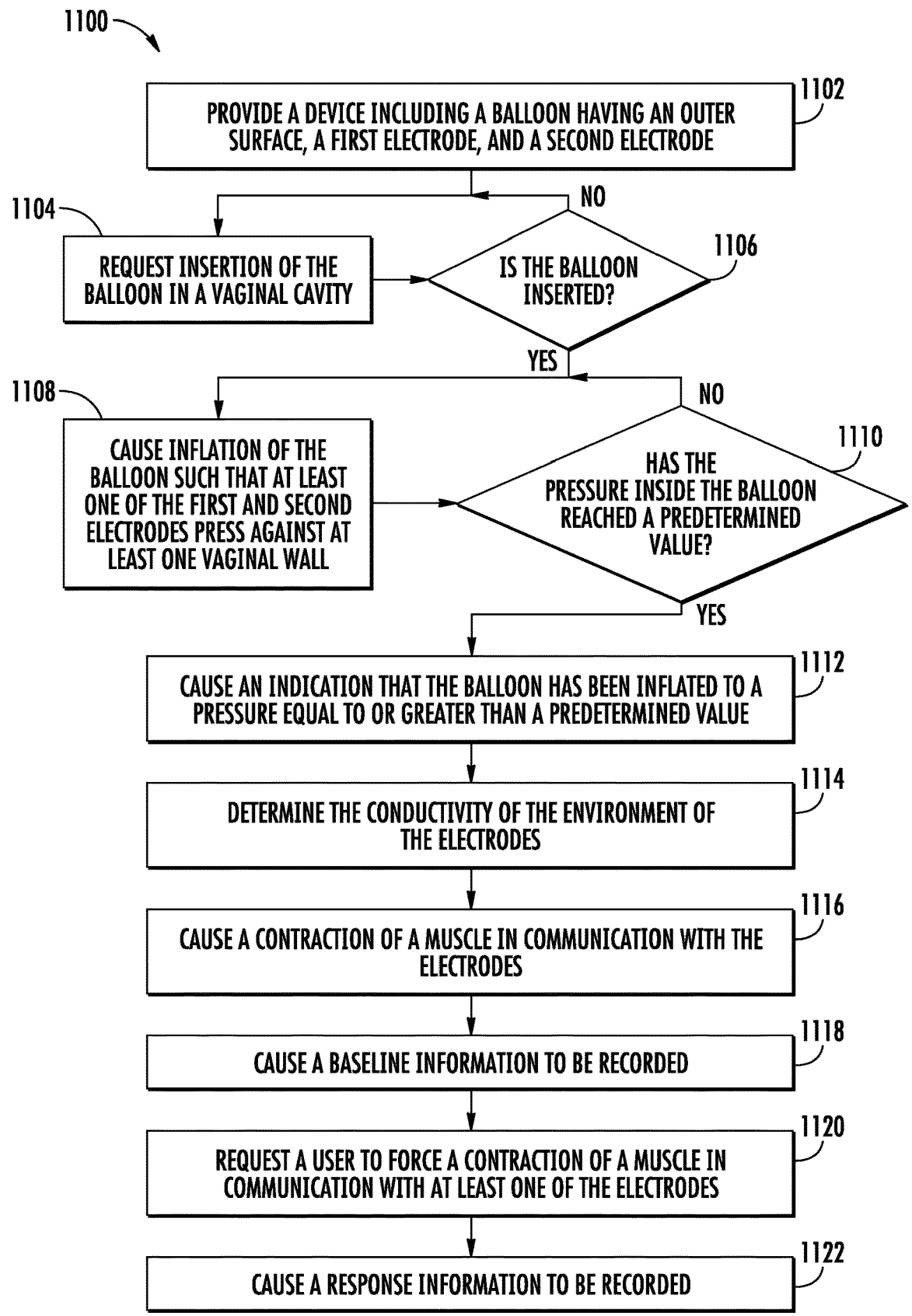
FIG. 12 is a schematic flow chart of a process for treating urinary incontinence using the medical device of FIG. 1, shown according to another exemplary embodiment.

Referring to FIG. 12, a flowchart of process 1100 for treating urinary incontinence is shown according to an exemplary embodiment. Process 1100 is shown to include the steps of providing a device as described above and including a balloon having an outer surface, a first electrode, and a second electrode (step 1102). Process 1100 further includes the step of requesting insertion of the balloon into a vaginal cavity (step 1104), for example, by indicating that device 100 is initialized and ready for insertion (e.g., illuminating in indicator lamp 150), providing an aural request through audio device 714, or providing instructions along with providing probe assembly 102. The determination of insertion may be an inference by processing electronics 800 (e.g., by position module 938) or by a confirmation from a user through control inputs 144. If the balloon is not inserted (step 1106) then process 1100 returns to step 1104. According to an alternate embodiment, if the balloon is not inserted, then step 1106 may return to itself waiting for determination that the balloon has been inserted (e.g., dwelling).

If the balloon has been inserted (step 1106), process 1100 causes inflation of the balloon such that at least one of the first and second electrodes press against at least one vaginal wall (step 1108). According to various embodiments, step 1108 may include requesting a user to actuate pump 156, causing actuation of pump 156, and/or causing operation of a motorized pump. If the pressure inside the balloon has not reached a predetermined value (step 1110) then process 1100 returns to step 1108. Alternatively, if the pressure inside the balloon has not reached a predetermined value within a threshold time, process 1100 may proceed to an error process (not shown) which may cause an indication of error. If the pressure inside the balloon has reached a predetermined value (step 1110), then process 1100 causes an indication that the balloon has been inflated to a pressure equal to or greater than a predetermined value (step 1112). According to various embodiments the indication may be visual, aural, or haptic. Process 1100 may further include the step of determining the conductivity of the environment of the electrode (step 1114). For example, a conductivity sensor in probe 120 may determine the effects of vaginal fluids or lubricants have on the conductivity of the probe environment. The conductivity sensor may measure the resistivity between electrodes 128 or measure the current delivered for a provided voltage. According to one embodiment, a low voltage (e.g., 2 Volts) is provided across electrodes 128, the resulting current is measured, and resistance is calculated.

Process 1100 is further shown to include the steps of causing a contraction of a muscle in communication with the electrodes (step 1116) and causing a baseline information to be recorded (step 1118). Baseline information may be information from sensors 802 measured at a point in time after the balloon has been inserted and the pressure in the balloon has reached a threshold value and no current or voltage is passing through electrodes 128. Process 1100 is further shown to include the steps of requesting a user to manually or volitionally force a contraction of a muscle in communication with at least one of the electrodes (step 1120) and causing a response information to be recorded (step 1122). Steps 1120 and 1122 enable tracking of the user's progress. The recorded data may be provided to a healthcare professional or reviewed by the user. Providing data to a healthcare professional may include reviewing data directly from display 148 on controller 104, uploading the data from controller 104 to a computer, or transmitting the response information across the Internet to a computer (e.g., a server).

Various alternate embodiments of the process described are contemplated. For example, the order of steps may be changed, e.g., determining if the balloon is inserted (step 1106) may be a prerequisite to, or occur simultaneously with, determining the conductivity of the environment of the electrode (step 1114). According to another embodiment, causing a baseline information to be recorded (step 1118) may occur before causing a contraction of the muscle in communication with the electrodes (step 1116). Process 1100 may not include all of the steps listed. For example, process 1100 may not include the steps of requesting insertion of the balloon into a vagina (step 1104) or determining if the balloon has been inserted (step 1106). According to another embodiment, process 1100 does not include the step of determining the conductivity of the environment of the electrode (step 1114). According to various other embodiments, process 1100 may not include the steps of causing a baseline information be recorded (step 1118), requesting a user to force a contraction of a muscle in communication with at least one of the electrodes (step 1120), or causing a response information to be recorded (step 1122). Process 1100 may include additional steps, e.g., lubricating the balloon, inserting the uninflated balloon in a vaginal cavity, deflating the balloon, and/or removing the balloon from the vaginal cavity.

According to another embodiment, process 1100 may output an indication of the response information, for example, outputting a value corresponding to the strength of the force contraction by illuminating a portion of the sequentially oriented lamps 146, displaying a pressure, and/or displaying a normalized strength value, e.g., on a 1-10 scale.

Data recorded during process 1100 (e.g., electrical signals received from electrodes 128a and 128b or pressure sensor 804) may be provided to a healthcare professional and/or reviewed by a user. Reviewing data by the user may include wirelessly transmitting data from controller 104 to a server or device of a user (e.g., smartphone, tablet, laptop, personal computer). In such embodiments, the controller 104 includes a wireless transmission device configured to transmit information via any wireless communications protocol (e.g., Bluetooth, Wi-Fi, etc.). In some embodiments, the device for viewing the transmitted information is a smartphone or computer. Processing electronics 800 can be configured to generate a variety of graphical data including graphs, charts, and tables to be reviewed by the user. A user may then view the data through an application or web interface to track performance and usage of the medical device 100. For example, a user may be able to view data corresponding to pelvic muscle contraction strength over a selected time interval (e.g., 7 days, 14 days, 30 days, etc.). If the user discovers that muscle contraction strength is not improving as desired, the user may contact a healthcare professional or adjust the operation of device 100 in an attempt to achieve better results.

Providing data to a healthcare professional may include wirelessly transmitting data (e.g., via the Internet, Bluetooth, etc.) from controller 104 via the wireless transmission device to a server or device. In some embodiments, data is wirelessly transmitted to a common server that can be accessed by both the user and healthcare professionals. A web application or other type of web interface can allow a healthcare professional to access data related to patient incontinence treatment without having to meet with the patient or download specialized software. A healthcare professional can provide feedback and make adjustments to a patient's treatment plan based on this data. For example, a healthcare professional may be able to view a trend of the user using the medical device 100, and the trend can indicate the strengthening of the user's pelvic floor muscles. In another example, if a user is not showing significant improvement in muscle contraction strength, the healthcare provider can make adjustments to configuration data 924 of a device 100 associated with that user. The ability of device 100 to wirelessly transmit data in this manner can allow for a more user-friendly experience as well as more effective treatment of urinary incontinence.

It is important to note that the construction and arrangement of the elements of the devices as shown in the exemplary embodiments are illustrative only. Although only a few embodiments of the present disclosure have been described in detail, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements. It should be noted that the elements and/or assemblies of the enclosure may be constructed from any of a wide variety of materials that provide sufficient strength or durability, in any of a wide variety of colors, textures, and combinations. Additionally, in the subject description, the word "exemplary" is used to mean serving as an example, instance or illustration. Any embodiment or design described herein as "exemplary" is not necessarily to be construed as preferred or advantageous over other embodiments or designs. Rather, use of the word exemplary is intended to present concepts in a concrete manner. Accordingly, all such modifications are intended to be included within the scope of the present inventions. Other substitutions, modifications, changes, and omissions may be made in the design, operating conditions, and arrangement of the preferred and other exemplary embodiments without departing from the spirit of the appended claims. Any means-plus-function clause is intended to cover the structures described herein as performing the recited function and not only structural equivalents but also equivalent structures.

The present disclosure contemplates methods, systems and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

Although the figures may show a specific order of method steps, the order of the steps may differ from what is depicted. Also, two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps. Other substitutions, modifications, changes and omissions may be made in the design, operating configuration, and arrangement of the preferred and other exemplary embodiments without departing from the spirit of the appended claims.

What is claimed is:

1. An apparatus for the treatment of urinary incontinence comprising:
    a probe comprising:
        a balloon configured for movement between an inflated state and a deflated state, the balloon comprising bellows;
        an electrode coupled to an outer surface of the balloon, the electrode configured to transmit an electrical pulse to cause a contraction of a muscle in communication with the electrode; and
        an internal cavity defined by the balloon; and
    a control device configured to be operable by a user to cause the balloon to selectively move between the inflated state and the deflated state and to cause the electrode to transmit the electrical pulse;
    wherein the electrode provides exterior longitudinal support of the balloon by being integrally formed within a material of the balloon such that the bellows and the electrode are configured to cooperate to maintain the structural integrity of the balloon without a structural support element being located within the internal cavity, the bellows and the electrode further configured to cooperate to cause the balloon to inflate in a radially non-uniform manner.

2. The apparatus of claim 1, wherein the bellows comprise at least two folds extending outward from an interior of the balloon.

3. The apparatus of claim 1, wherein the bellows comprise at least three folds extending toward an interior of the balloon.

4. The apparatus of claim 1, wherein the bellows comprise at least two folds extending outward from an interior of the balloon, and wherein the bellows comprise at least three folds extending toward the interior of the balloon.

5. The apparatus of claim 1, wherein the bellows are configured to maintain the balloon in a substantially oval shape when the balloon is in a deflated state.

6. The apparatus of claim 1 comprising a pump in communication with the balloon and configured to cause inflation of the balloon such that the electrode may contact a vaginal wall of a user.

7. The apparatus of claim 1 comprising processing electronics configured to inhibit the electrode from causing a contraction of the muscle in communication with the electrode until the balloon has been inflated to a predetermined pressure.

8. The apparatus of claim 1 comprising processing electronics configured to cause an indication in response to a determination that a pressure inside the balloon has reached a predetermined value.

9. The apparatus of claim 1 comprising processing electronics configured to cause an indication in response to a determination that the balloon has been inflated to a pressure equal to or greater than a predetermined value.

10. The apparatus of claim 1 comprising processing electronics configured to cause inflation of the balloon.

11. The apparatus of claim 1 comprising processing electronics configured to cause a current of between 10 milliamps and 50 milliamps.

12. The apparatus of claim 1, wherein the electrode is a first electrode, and further comprising a second electrode coupled to an outer surface of the balloon and processing electronics configured to cause an electric potential difference between the first electrode and the second electrode.

13. The apparatus of claim 12, wherein the electric potential difference is between 0 and 80 Volts.

14. The apparatus of claim 12, wherein the electric potential difference is between 10 Volts and 50 Volts.

15. The apparatus of claim 12, wherein the processing electronics are configured to variably control the electric potential difference.

16. The apparatus of claim 1, wherein the material of the balloon between the electrode and the interior of the balloon is a first thickness, the material of the balloon of the bellows is a second thickness, and the first thickness is greater than the first second thickness.

17. The apparatus of claim 1, wherein the electrode provides exterior longitudinal support of the balloon by being positioned along a majority of a length of the balloon.

18. An apparatus for the treatment of urinary incontinence comprising:
    a probe comprising:

a balloon configured for movement between an inflated state and a deflated state, the balloon comprising bellows;

a first electrode coupled to a first outer surface of the balloon, the first electrode configured to transmit an electrical pulse to cause a contraction of a muscle in communication with the first electrode;

a second electrode coupled to a second outer surface of the balloon, the second electrode configured to transmit an electrical pulse to cause a contraction of a muscle in communication with the second electrode; and an internal cavity defined by the balloon; and a control device configured to cause the balloon to inflate such that the first electrode and the second electrode contact the muscle, and to cause the first electrode and the second electrode to transmit electrical pulses to the muscle;

wherein the balloon is substantially hollow, and wherein the electrode provides exterior longitudinal support of the balloon by being integrally formed within a material of the balloon such that the bellows, the first electrode, and the second electrode are configured to cooperate to maintain the structural integrity of the balloon without a structural support element being located within the internal cavity.

19. The apparatus of claim 18, wherein the bellows comprise at least two folds extending outward from an interior of the balloon, and wherein the bellows comprise at least three folds extending toward the interior of the balloon.

20. The apparatus of claim 18, wherein the bellows are configured to maintain the balloon in a substantially oval shape when the balloon is in a deflated state.

21. A method for treating urinary incontinence comprising:

providing a device comprising a probe, the probe comprising:

a balloon configured for movement between an inflated state and a deflated state, the balloon comprising bellows;

a first electrode coupled to a first outer surface of the balloon, the first electrode configured to transmit an electrical pulse to cause a contraction of a muscle in communication with the first electrode;

a second electrode coupled to a second outer surface of the balloon, the second electrode configured to transmit an electrical pulse to cause a contraction of the muscle in communication with the second electrode; and an internal cavity defined by the balloon;

causing, by a control device, the balloon to inflate such that the first electrode and the second electrode contact the muscle; and causing, by the control device, the first electrode and the second electrode to transmit electrical pulses to the muscle;

wherein the balloon is substantially hollow, and wherein the electrode provides exterior longitudinal support of the balloon by being integrally formed within a material of the balloon such that the bellows, the first electrode, and the second electrode are configured to cooperate to maintain the structural integrity of the balloon without a structural support element being located within the internal cavity.

\* \* \* \* \*